United States Patent
Olsson et al.

(10) Patent No.: US 7,037,902 B2
(45) Date of Patent: May 2, 2006

(54) AFFINITY SMALL MOLECULES FOR THE EPO RECEPTOR

(75) Inventors: Lennart Olsson, Orinda, CA (US); Tatjana Naranda, Mountain View, CA (US)

(73) Assignee: Receptron, Inc., Mountain View, CA (US)

( * ) Notice: Subject to any disclaimer, the term of this patent is extended or adjusted under 35 U.S.C. 154(b) by 34 days.

(21) Appl. No.: 10/613,754

(22) Filed: Jul. 2, 2003

(65) Prior Publication Data

US 2004/0171541 A1    Sep. 2, 2004

Related U.S. Application Data

(60) Provisional application No. 60/393,361, filed on Jul. 3, 2002, provisional application No. 60/393,360, filed on Jul. 3, 2002, provisional application No. 60/394,110, filed on Jul. 3, 2002.

(51) Int. Cl.
*C07K 14/505* (2006.01)

(52) U.S. Cl. .............................. 514/43; 514/2; 530/300

(58) Field of Classification Search ................ 530/300, 530/350, 380; 514/2
See application file for complete search history.

(56) References Cited

U.S. PATENT DOCUMENTS 4,546,104 A * 10/1985 Campbell et al. ........... 514/293
5,942,520 A *  8/1999 Pamukcu et al. ........... 514/293

OTHER PUBLICATIONS

SA Qureshi, et al. PNAS (1999) 96, 12156-12161.*
DL Boger and J Goldberg. Bioorg. Med. Chem. (2001) 9, 557-562.*
DM Wojchowski, et al. Exp. Cell Res. (1999) 253, 143-156).*
PA Tilbrook and SP Klinken Intl. J. Biochem. Cell Biol. (1999) 31, 1001-1005.*

* cited by examiner

*Primary Examiner*—Christopher R. Tate
*Assistant Examiner*—Andrew D. Kosar

(57) ABSTRACT

Compounds are provided that complex with the modulating domain of erythropoietin receptor (EPO-R) for use with EPO-R to determine the presence of EPO-R, the ability of other molecules to bind to the modulating domain in competitive assays and to induce a signal by EPO-R into a cell when bound by the subject compounds in a physiological environment. The compounds are characterized by having a six-membered heterocyclic ring comprising at least one nitrogen atom and include substituted triazolopyrimidine, pyridazinone, pyridine and piperidine.

30 Claims, 17 Drawing Sheets

FIGURE 1—Replacement of ERP with small molecule
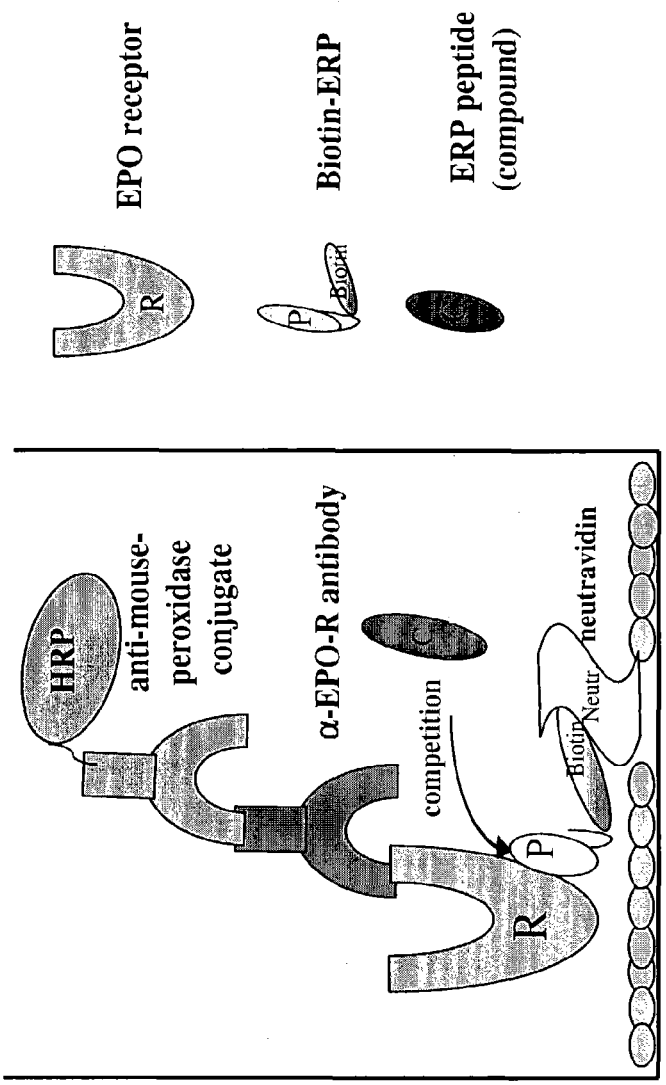

FIGURE 2--Role of small molecule in activation of EPO-R signaling pathway

Study of small molecule effects and potential applications

*In vitro studies*

- Erythroid system
  - Activation of proliferative and anti-apoptotic pathway(s)
  - Colony formation in fetal liver cells
  - CFU-e/BFU-e formation in bone marrow (mouse and human)
- CNS system
  - Activation of anti-apoptotic pathway
  - Survival of neural-like cells upon serum withdrawal

*In vivo studies*

- Effect in animals with carboplatin induced anemia; given I.p. and orally
- Reticulocytes levels in normal animals

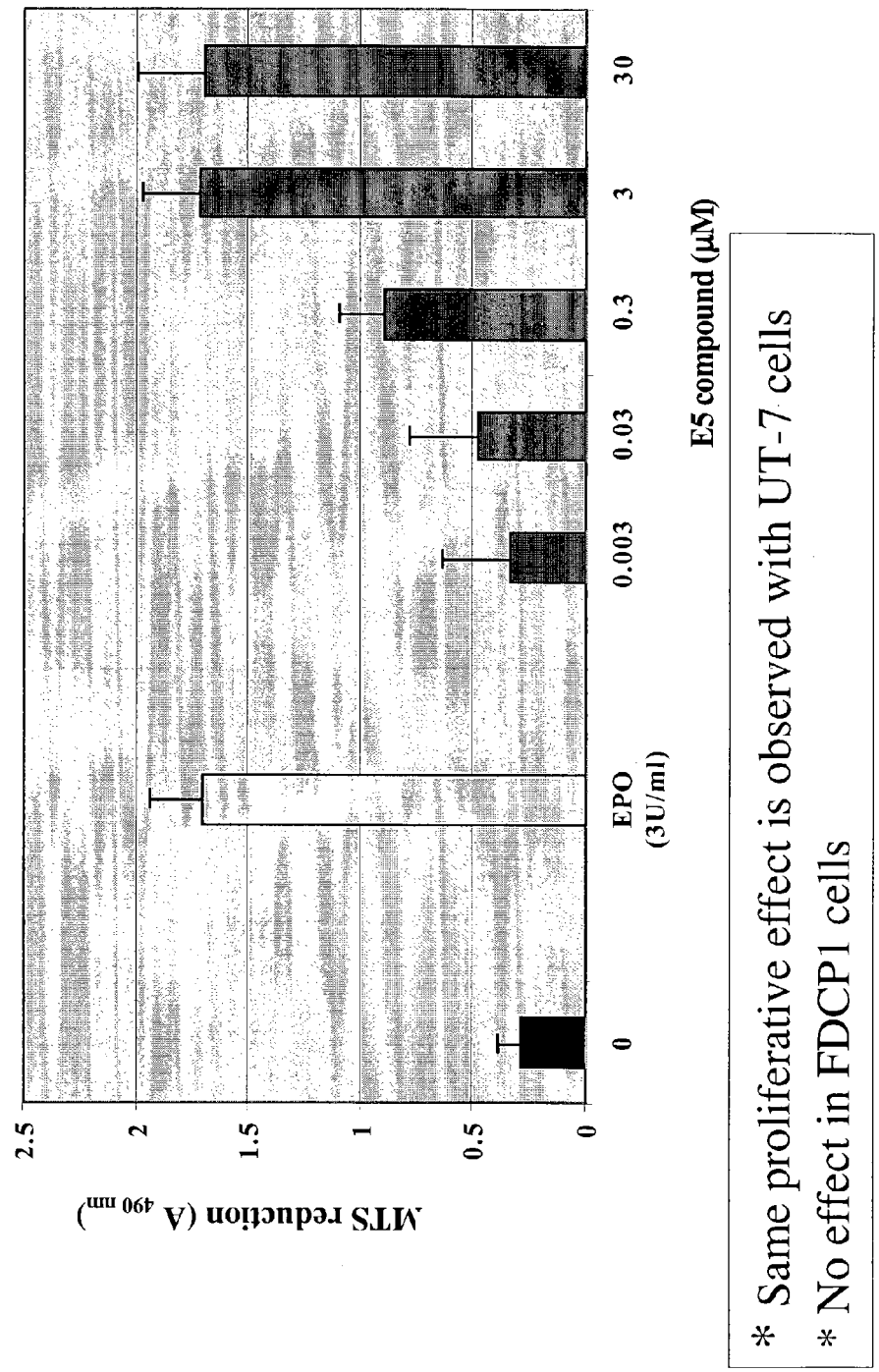
FIGURE 3 -- Proliferative effect of E5 compound in TF-1 cells
* Same proliferative effect is observed with UT-7 cells
* No effect in FDCP1 cells

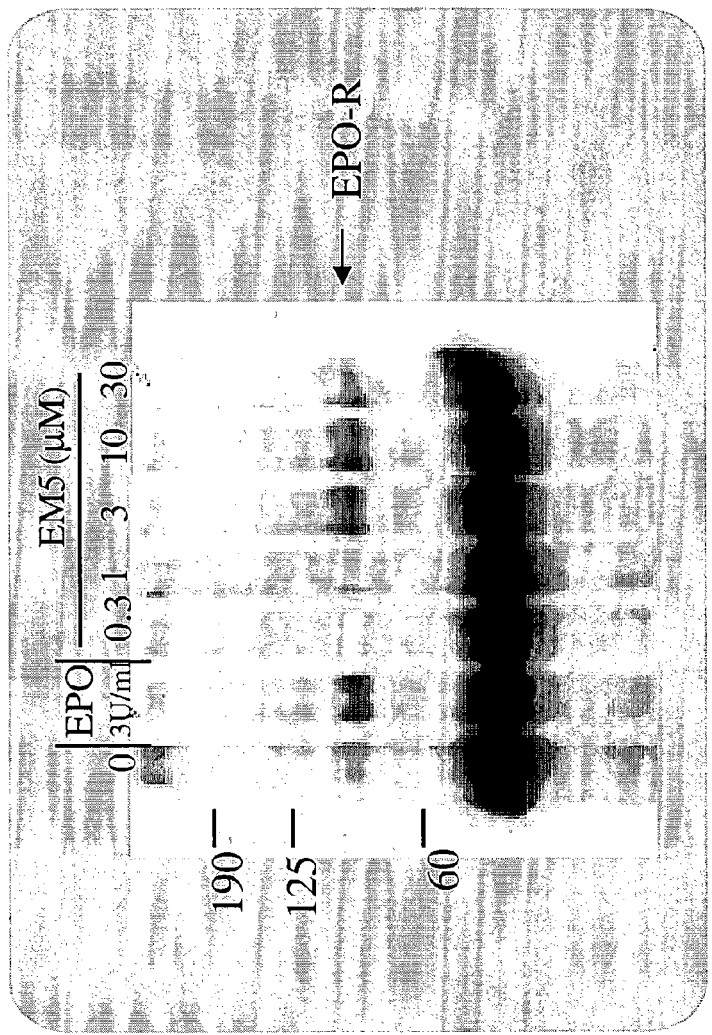
FIGURE 4 -- Activation of signaling cascade through EPO-R by small molecule
Small molecules bind to and activate/phosphorylate EPO-R (UT-7 cells)

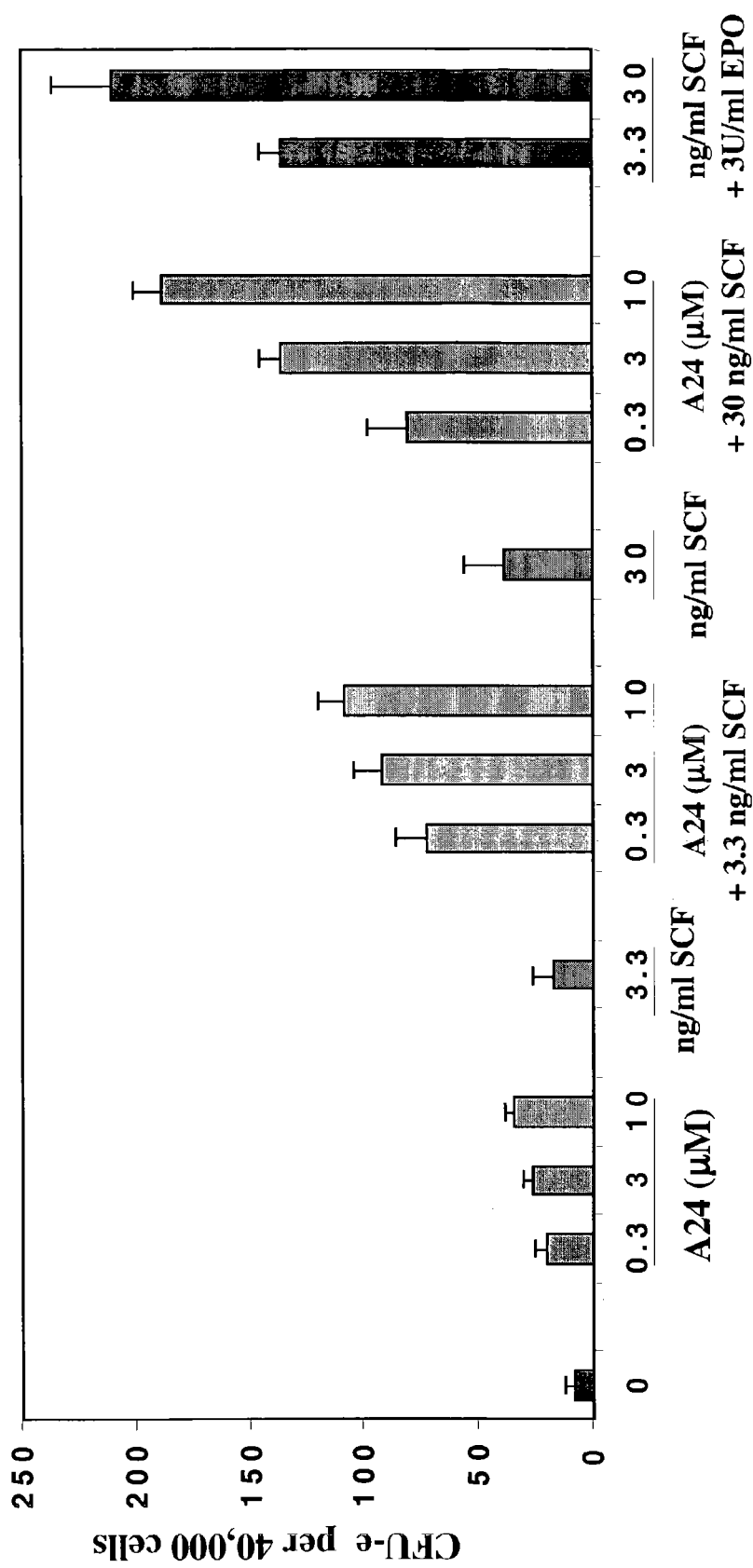
FIGURE 5--Small molecules promote colony formation in the presence of SCF Fetal liver cells (day 3)

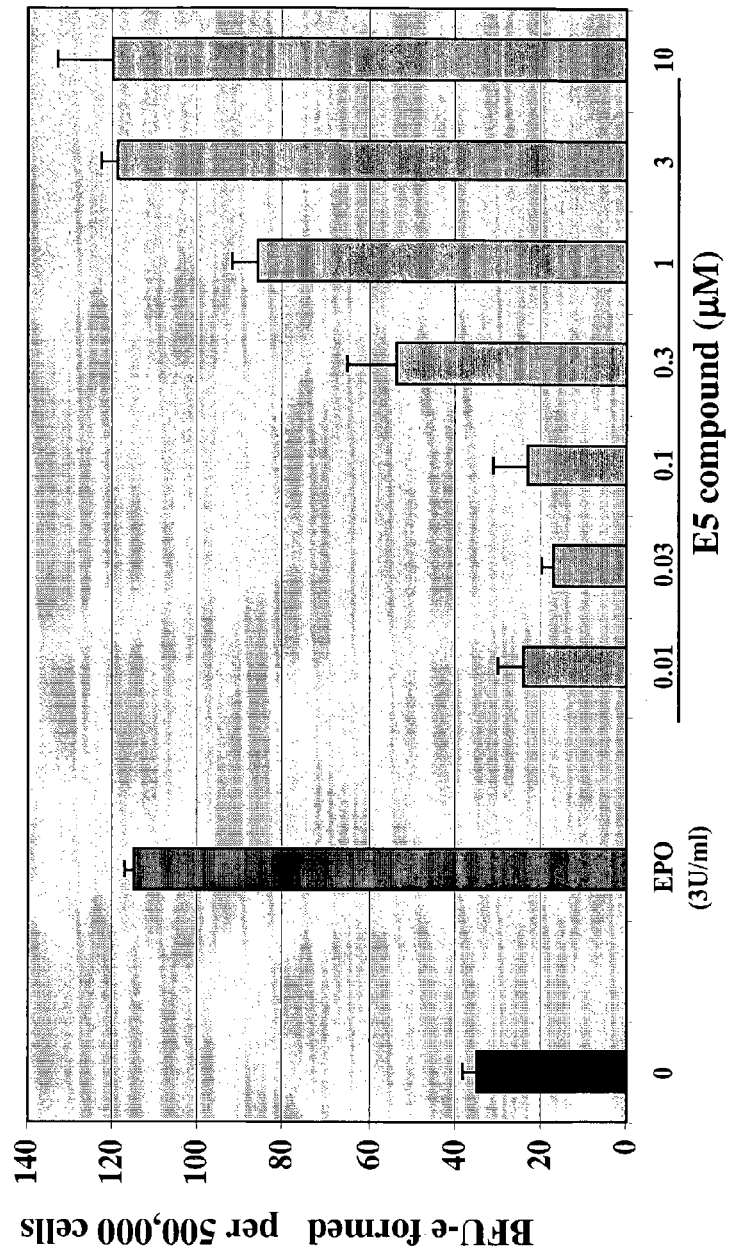
FIGURE 6--Effect of EPO-like small molecule on erythroid colony formation in methylcellulose
Human bone marrow

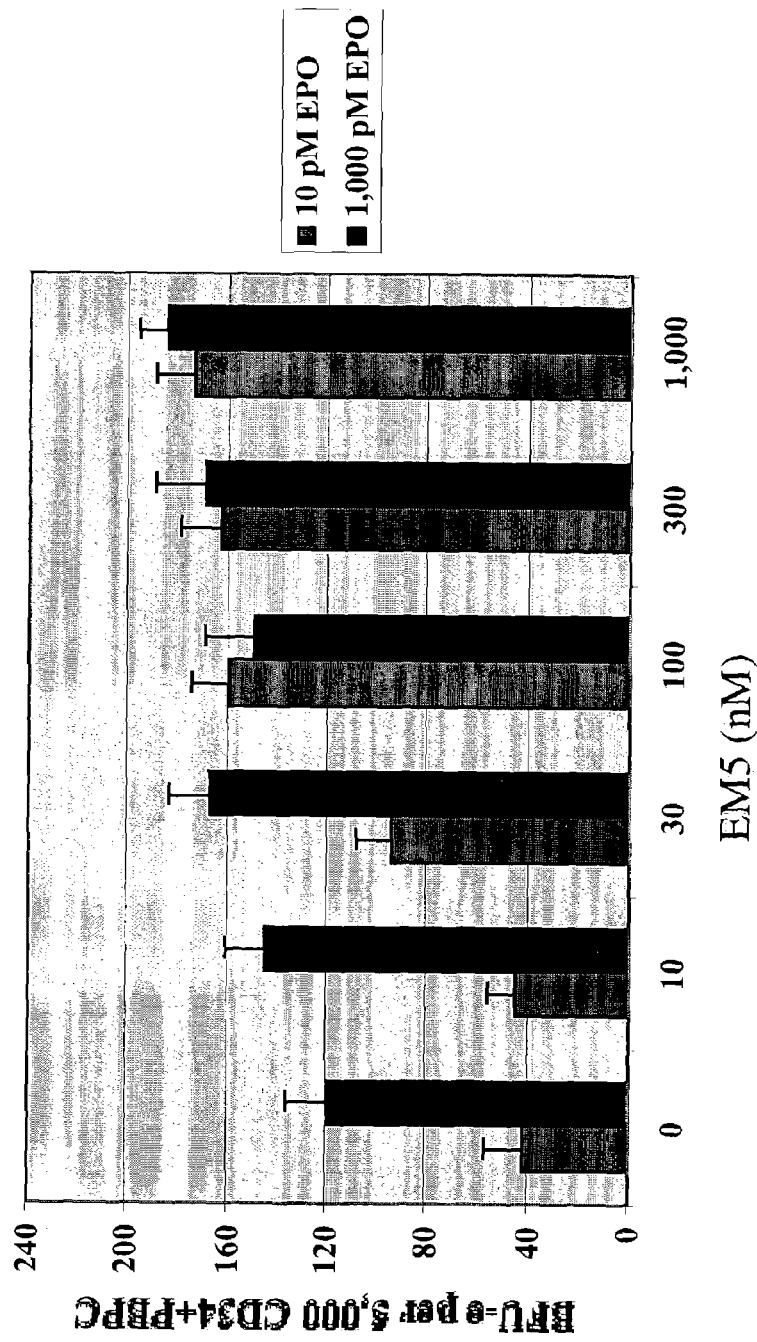
FIGURE 7 -- Synergy between EM5 small molecule and EPO on erythroid colony formation Human bone marrow

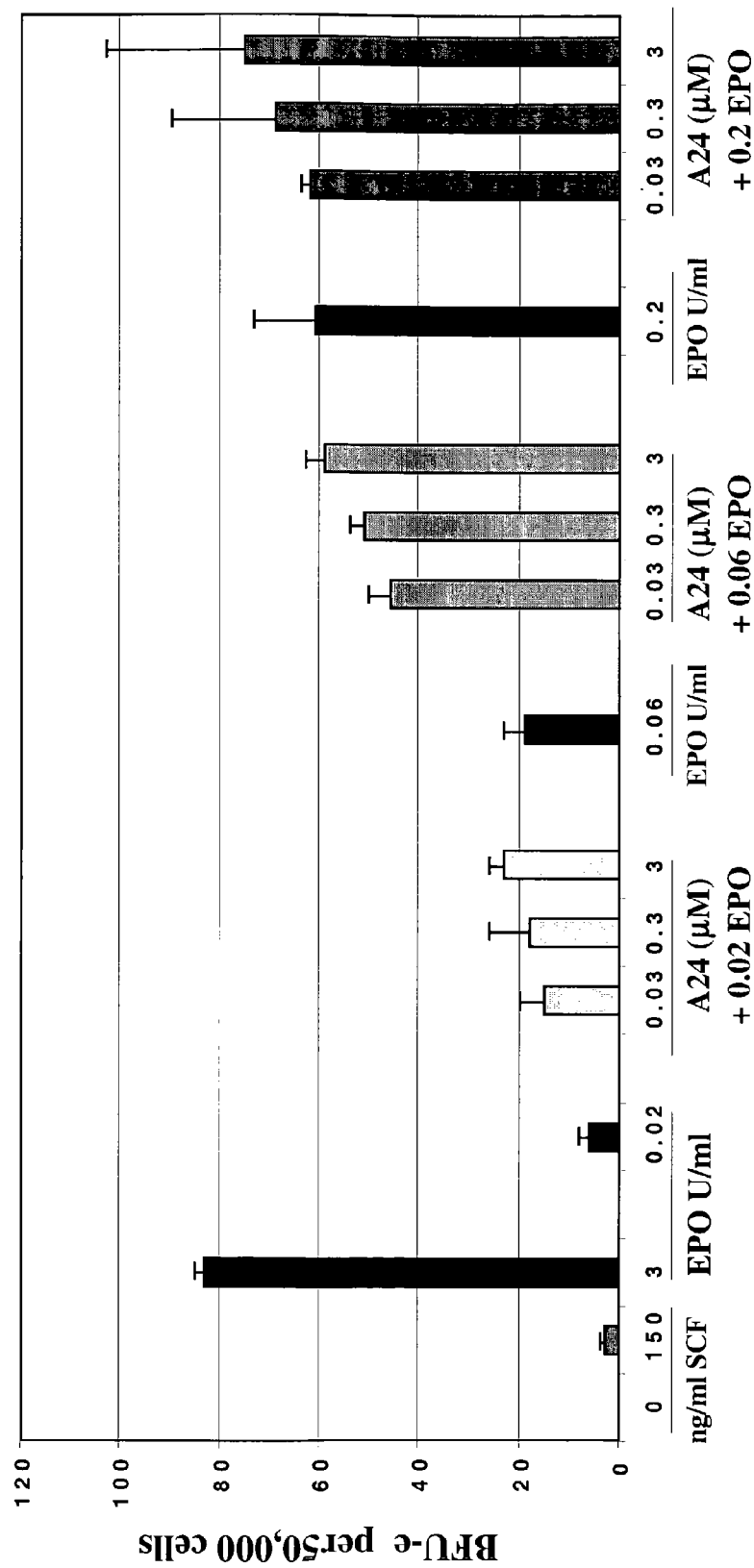

EFFECT OF EPO-LIKE ACTIVITY, SMALL MOLECULE - ON HEMATOCRIT IN 8 WEEK OLD C57BL MALE MICE

Dose-response

SYNERGISTIC EFFECT ON CARBOPLATIN-INDUCED ANEMIA BY ERYTHROPOIETIN WITH EPO SMALL MOLECULE E6 IN 8 WEEK OLD MALE C57BL MICE DAY 10

EFFECT OF E6 ADMINISTERED BY GAVAGE ON HEMATOCRIT IN 8 WEEK-OLD MALE C57BL/J MICE

Effect of EPO - small molecule on reticulocyte levels in normal animals

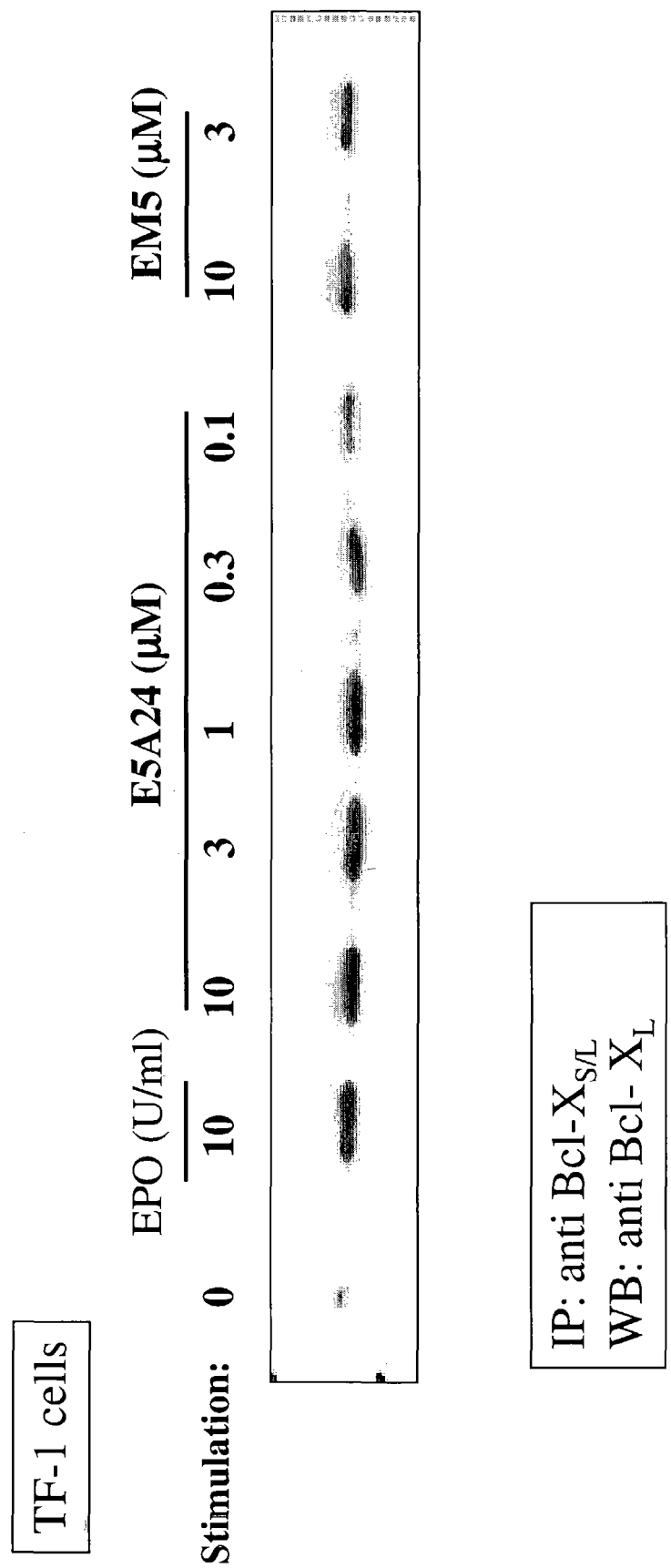
FIGURE 13 -- Small molecule activates Bcl-$X_L$ expression

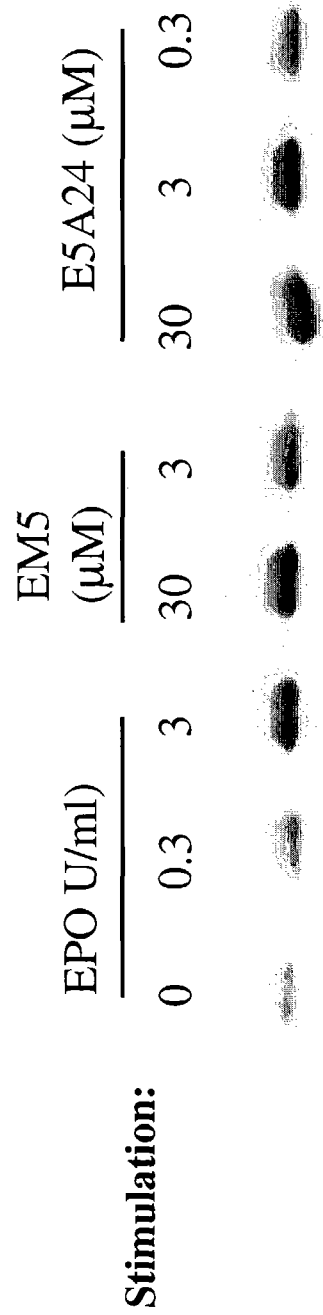
FIGURE 14 — Small molecules activate Bcl-$X_L$ expression

FIGURE 15 -- Effect of small molecules on P19 cells
- P-19 is a neural-like embryonal carcinoma cell line that undergoes apoptosis upon withdrawal of serum
Protocol:
* Treatment with small molecule or EPO 24 hrs prior to serum withdrawal
* Serum withdrawal for 48 hours ± EPO or small molecule
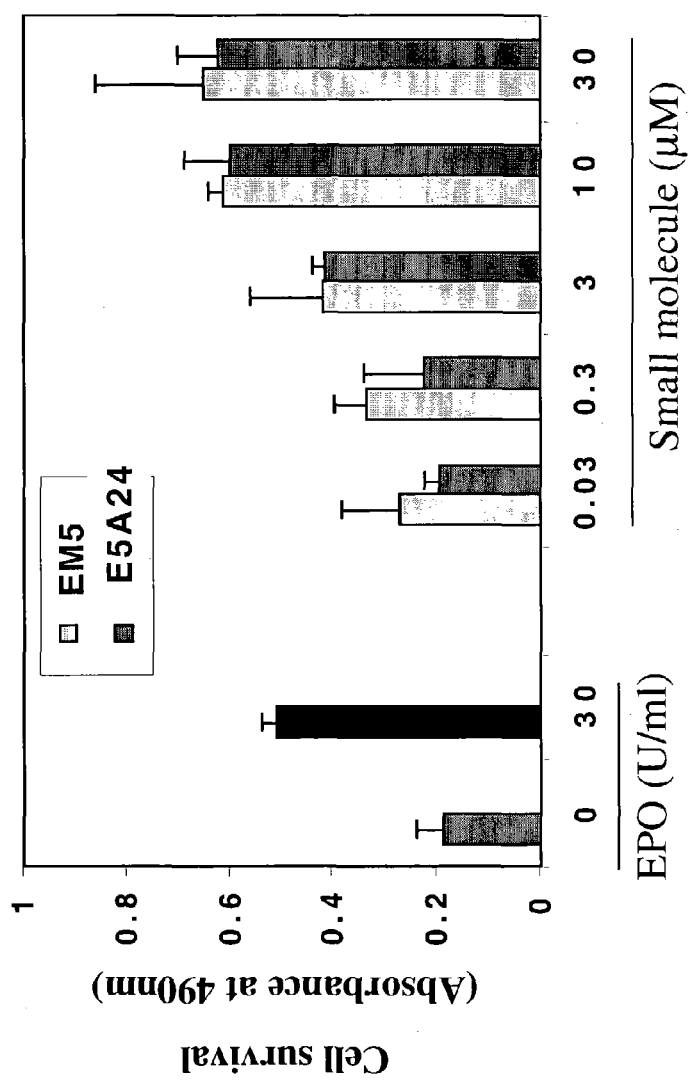

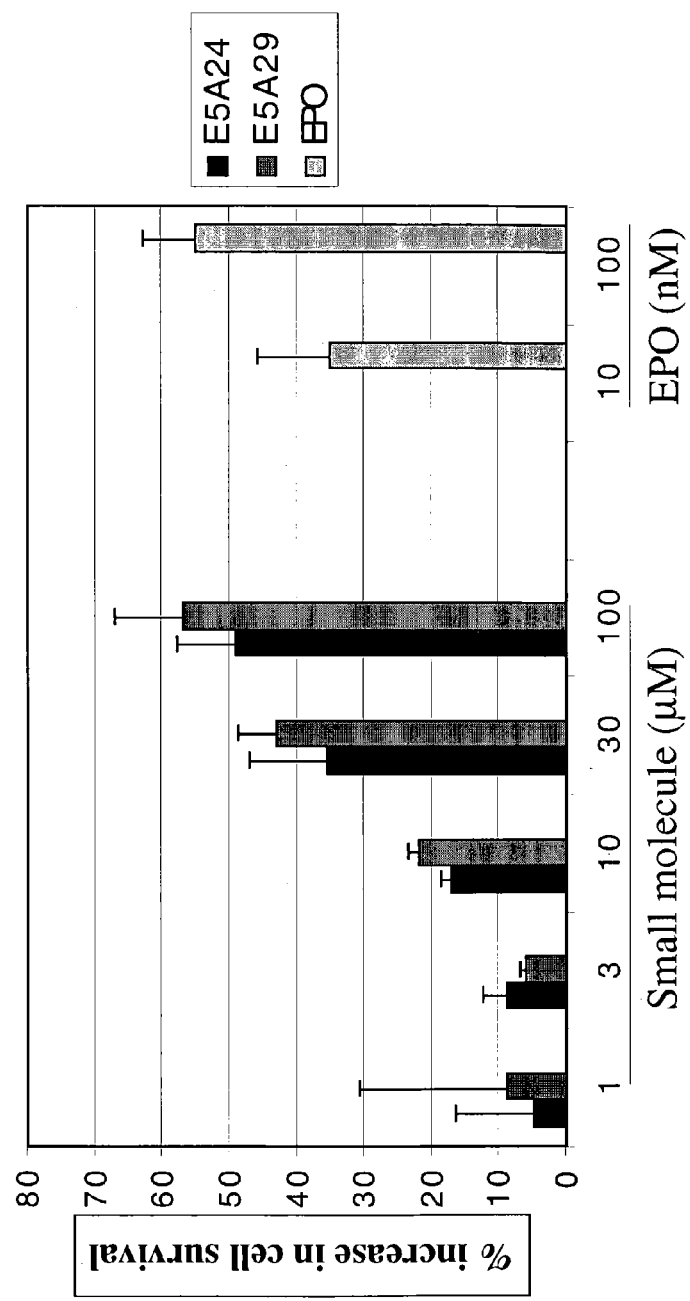
FIGURE 16 -- Small molecules prevent neuronal apoptosis after glutamate challenge
* Cortical Neurons isolated from Embryonic day 18 rats
* Treatment with small molecule or EPO for 24 hrs
* Challenge with 300 μM Glutamate for 24 hrs

FIGURE 17 -- Characteristics of EPO-like activity small molecules

➢ Bind to EPO-R and Activate EPO-R signaling pathway in the presence and absence of hormone
  – Bind to different site than hormone and do not interfere with EPO binding ➢ Act on early erythroid progenitors
  – CFU-e/BFU-e formation in fetal liver cells
  – Synergistic effect with EPO in Bone marrow cells (mouse and human)

➢ Promote EPO like anti-apoptotic activity
  – Expression of Bcl-$X_L$ protein
  – Increase in neuronal survival during glutamate challenge ➢ Restore hematocrit level in *in vivo* animal model, given I.P. and orally
  – Act in synergy with EPO ➢ Increase reticulocyte levels in normal animals ial portion of the administered EPO is lost. Despite these problems, the dramatic effect achieved by EPO has resulted in annual sales exceeding a billion dollars.

SEQUENCE LISTING

```
<160> NUMBER OF SEQ ID NOS: 2

<210> SEQ ID NO 1
<211> LENGTH: 23
<212> TYPE: PRT
<213> ORGANISM: Homo sapiens

<400> SEQUENCE: 1

Gln Arg Val Glu Ile Leu Glu Gly Arg Thr Glu Cys Val Leu Ser Asn
1               5                   10                  15

Leu Arg Gly Arg Thr Arg Tyr
            20

<210> SEQ ID NO 2
<211> LENGTH: 23
<212> TYPE: PRT
<213> ORGANISM: Homo sapiens

<400> SEQUENCE: 2

Gln Arg Val Glu Val Leu Glu Gly Arg Thr Glu Cys Val Leu Ser Asn
1               5                   10                  15

Leu Arg Gly Gly Thr Arg Tyr
            20
```

AFFINITY SMALL MOLECULES FOR THE EPO RECEPTOR

CROSS-REFERENCE TO RELATED APPLICATIONS

This application is a continuation of provisional patent applications, Nos. 60/393,361; 60/393,360 and 60/394,110, all filed on Jul. 3, 2002, the entire contents of each of which is incorporated herein by reference

STATEMENT TO COMPUTER DISK AND SEQUENCE LISTING

This application includes a sequence listing of 2 sequences and a computer disk labeled "Sequence Listing for application entitled "Affinity Small Molecules for the EPO Receptor" by Lennart Olsson and Tatjana Naranda" containing files "REC104-SEQLIST.prj" dated "Jul. 2, 2003" with 990 bytes, which is the PatentIn project file generated using PatentIn Version 3.0 software provided by the USPTO, and "REC104-SEQLIST.doc", dated "Jul. 2, 2003" with 21 kilobytes, which is the generated sequence listing from the PatentIn project file REC104-SEQLIST.prj using PatentIn Version 3.0 software, all which are herein incorporated. The information recorded in computer readable format on the incorporated computer disk labeled "Sequence Listing" containing files "REC104-SEQLIST-.prj" and "REC104-SEQLIST.doc" are identical to the incorporated written sequence listing

BACKGROUND OF THE INVENTION

1. Field of the Invention

The invention relates generally to non-peptide molecules having affinity for the erythropoietin receptor at a modulating site that is other than the erythropoietin binding site and the use of such molecules.

2. Background Information

As the cellular pathways are discovered, there is increasing insight into the different molecules that are involved in the transduction of a signal resulting from the binding of a ligand to a cellular membrane receptor to the transcription and expression of genes in the host cell genome. The development of erythropoietin ("EPO") has allowed for the substantial improvement in the treatment of anemia. Anemia may be a natural phenomenon resulting from a genetic defect or may be as a result of infection or treatment with radiation or chemotherapy. In each of these instances it is necessary for the viability of the host that the red blood cell count or hematocrit remain substantially normal. In many situations, the level of treatment is compromised by the adverse effect on the red blood cell count, so that the desired therapy cannot be administered. The availability of EPO has provided a means for restoring the red blood cell count in compromised patients.

EPO is a large glycosylated protein that is expensive and difficult to manufacture, purify and formulate. It is also degraded by proteases when in the blood, so that a substantial portion of the administered EPO is lost. Despite these problems, the dramatic effect achieved by EPO has resulted in annual sales exceeding a billion dollars.

In U.S. Pat. No. 6,333,031 and in *Activation of erythropoietin Receptor Through a Novel Extracellular Binding Site*, Naranda, et al Endocrinology 2002 143(6):2293–2302; *Activation of Erythropoietin Receptor in the Absence of Hormone by a Peptide That Binds to a Domain Different from the Hormone Binding Site*, Naranda, et al., Proc. Natl. Acad. Sci. 1999, 96(13):7569–74 are reported the existence of an extracellular binding site of the EPO receptor ("EPO-R") referred to as the "modulation domain." In the human EPO-R, the modulation domain corresponds to about amino acids 194–216 and has the amino acid sequence QRVEI-LEGRTECVLSNLRGRTRY (SEQ ID NO:1). Binding of a 23 amino acid peptide having the sequence SEQ ID NO:1 to the EPO-R modulating domain resulted in modulation of the activity of the EPO-R in the presence or absence of the ligand. The peptide, therefore, offers an auxiliary compound for use with EPO to enhance thje activity of EPO and reduce the requirement for EPO to achieve analogous activity. The peptide can be readily synthesized efficiently and economically. However, the peptide is small and will be rapidly degraded in the blood. Also, it suffers from the inconvenience of requiring injection.

There is, therefore, an interest in developing small non-peptide molecules that can serve in conjunction with EPO in the treatment of anemia, as well as in other functions associated with assays for EPO-R, studying EPO and EPO-R function, purification of EP0-R, and analogous uses.

Relevant Literature

U.S. Pat. No. 6,333,031 and in Activation of Erythropoietin Receptor Through a Novel Extracellular Binding Site, Naranda, et al Endocrinology 2002 143(6):2293–2302; Activation of Erythropoietin Receptor in the Absence of Hormone by a Peptide That Binds to a Domain Different from the Hormone Binding Site, Naranda, et al., Proc. Natl. Acad. Sci. 1999, 96(13):7569–74, describe the modulation domain and SEQ ID NO:1. PCT/US02/064211 describes triazolopyrimidines for use as thrombin inhibitors.

SUMMARY OF THE INVENTION

Organic compounds having an azaaryl heterocyclic core and having at least 2 substituents are provided that find use as EPO-R modulating compounds, competing with SEQ ID NO:1 for the modulating domain site. The compounds can be used to bind to EPO-R for modulating the activity of the EPO-R, isolating EPO-R, evaluating the activity of compounds capable of upregulating the expression of EPO-R or its endocytosis, as well as other applications associated with affinity binding. Methods of preparation of the compounds are provided. The compounds are provided in combination with a polypeptide comprising the modulating domain of EPO-R, or instructions for use to bind EPO-R for assays, EPO-R modulation and EPO-R purification.

BRIEF DESCRIPTION OF THE DRAWINGS

FIG. 1 shows a graphical representation of a competitive binding assay that may be used to identify non-peptide EPO-R binding molecules.

FIG. 2 shows a summary of the methods used for assessment of non-peptide EPO-R modulators biological activity.

FIG. 3 shows a graph of the proliferative effect of non-peptide EPO-R modulator E5 in TF-1 cells.

FIG. 4 shows non-peptide EPO-R modulator E5 activation of EPO-R in UT-7 cells.

FIG. 5 shows the effect of non-peptide EPO-R modulator E5A24 on erythroid colony formation in methylcellulose. Fetal liver cells were isolated and seeded in the presence of compound. The colonies were counted on day 3.

FIG. 6 shows the effect of non-peptide EPO-R modulator E5 on erythroid colony formation in methylcellulose. Human bone marrow cells were isolated and seeded in the presence of compound. The colonies were counted on day 14.

FIG. 7 shows the cooperation between non-peptide EPO-R modulator E5 and EPO on erythroid colony formation in methylcellulose. CD34⁺ cells were isolated and seeded in the presence of compound. The colonies were counted on day 14.

FIG. 8 shows cooperation between non-peptide EPO-R modulator EM5A24 and EPO on erythroid colony formation in methylcellulose. Human bone marrow cells were isolated and seeded in the presence of compound. The colonies were counted on day 14.

FIG. 13 shows the effect of non-peptide EPO-R modulators E5A24 and EM5 on up-regulation of Bcl-$x_l$ expression in TF-1 cells.

FIG. 14 shows the effect of non-peptide EPO-R modulators E5A24 and EM5 on up-regulation of Bcl-$x_l$ expression in UT-7 cells.

FIG. 15 shows the effect of non-peptide EPO-R modulators E5A24 and EM5 on increased cell viability of P19 cells after the withdrawal of serum.

FIG. 16 shows the effect of non-peptide EPO-R modulators E5A24 and E5A29 on increased cell survival of cortical neurons after glutamate challenge.

FIG. 17 shows a summary of activity for non-peptide EPO-R modulators.

DETAILED DESCRIPTION OF THE INVENTION

Figure 9:
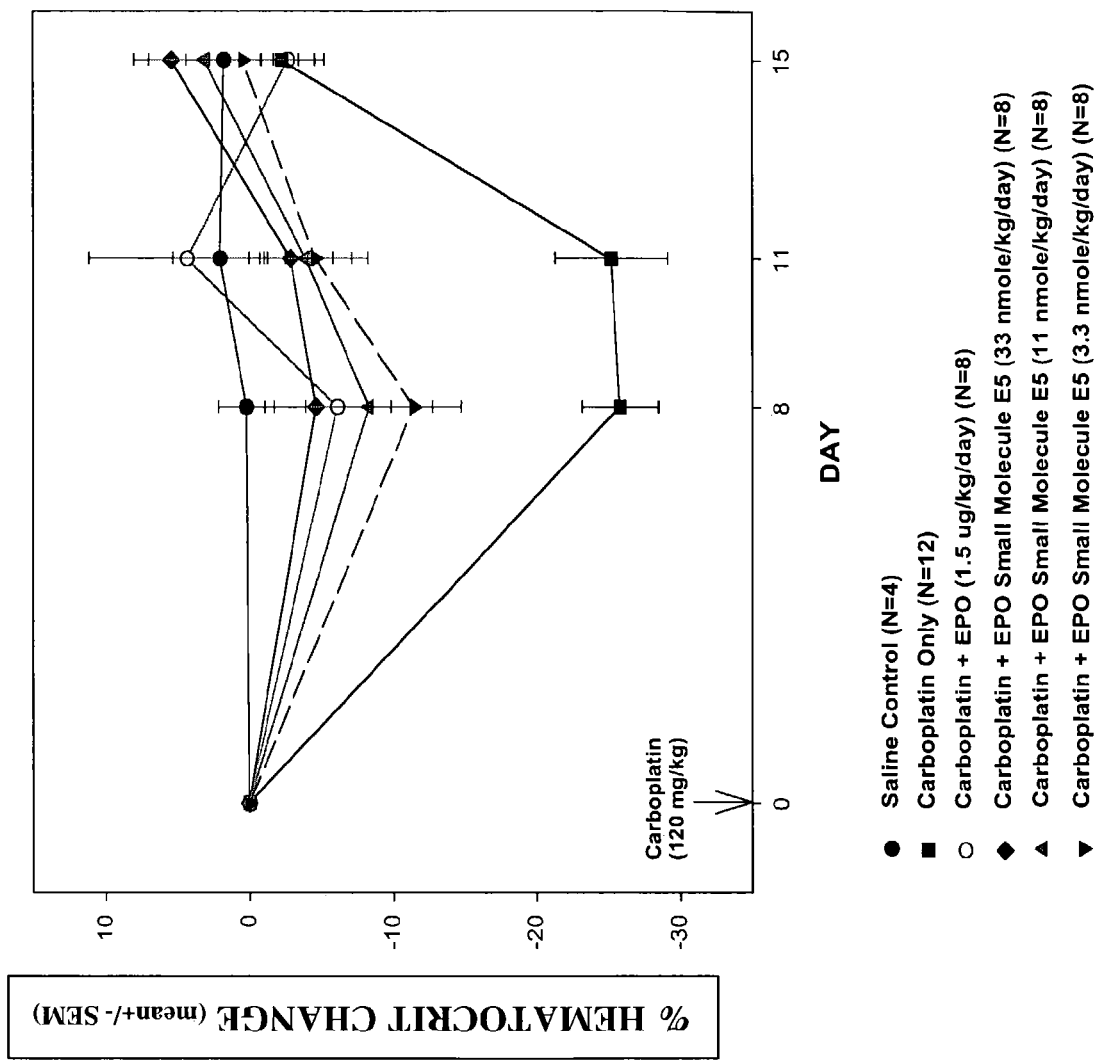
FIG. 9 shows the effect of non-peptide EPO-R modulator E5 on hematocrit levels in carboplatin-treated 8 week old C57BL mice. The compound was given i.p.

Organic compounds, having a substituted azaheterocycle of 6 annular members with from 1–2 nitrogen atoms in the ring, usually having at least one site of unsaturation, including azaaryl, as the core, are provided for binding to EPO-R at what is referred to as the "modulating domain." The compounds have at least two substituents and at least two rings, which may be fused, unfused or both. There will be at least one heterocyclic ring and up to 4 rings, where an aromatic ring substituent may be carbocyclic or heterocyclic and of 5–6 annular members. The substituents may be bonded to an annular carbon atom by a carbon atom or heteroatom. The compounds will have at least 12 atoms other than hydrogen and beside the core may contain aliphatic, aromatic, alicyclic, heterocyclic, and heterosubstituents.

The azaheterocycle that forms the core of the subject organic compounds will be substituted with various substituents, which substituents include aliphatic groups including carbocyclic group, aromatic groups and heterocyclic groups, both aromatic and non-aromatic. These in turn may be further substituted with various groups. Among the monovalent groups are included halo, CN, OH, OCH₃, NO₂, SH, NH₂, CF₃, alkyl e.g. CH₃, which in turn may be substituted with the indicated monovalent substituents other than alkyl. Divalent substituents will usually be bonded to a ring to form a fused ring, generally having 4 carbon atoms and forming a 6-membered carbocyclic ring with the adjacent annular atoms to which the divalent susbtituent is attached, wherein such ring may be further substituted with any of the substituents indicated above, including a divalent susbtituent.

The subject compounds can be provided in combination with a polypeptide comprising the modulating domain, a portion of the extracellular portion of EPO-R, EPO-R in purified form or in conjunction with other compounds, as a microsome, lysate, a mixture of polypeptides and/or organic molecules other than polypeptides. The subject compounds can be provided as separate from the modulating domain or bound to the modulating domain to form a complex. The compounds are provided in combination with a polypeptide comprising the modulating domain of EPO-R, or instructions for use to bind EPO-R for assays, EPO-R modulation and EPO-R purification.

The modulating domain is described in the literature as SEQ ID NO:1 for the human EPO-R ("hEPO-R") and the analogous sequence QRVEVLEGRTECVLSNLRGGTRY (SEQ ID NO:2) for the mouse EPO-R ("mEPO-R"), where these peptides bind to the modulating domain and affect the activity of the EPO-R in the presence of EPO binding to the EPO-R. (The peptides will hereafter be referred to as "ERP".) The sequences are reported in the art, Swissprot accession no. P19235 and P14753, respectively. For the most part, the modulating domains from different species will be highly conserved, generally differing by fewer than about 5 amino acids. Cross-reactivity is observed between the peptides, where the modulating domain peptide from one species will bind to an EPO-R receptor from a different species.

In referring to the EPO-R receptor is intended any mammalian EPO-R, particularly primate, more particularly human, rodentiae, murine, hamster and rat, or domestic animals, e.g. bovine, equine, porcine, etc.

The subject compounds share common features in having a heterocycle core of 6 annular atoms, having at least one nitrogen annular heteroatom and at least two substituents and/or a fused ring. The heterocyclic core includes triazolopyrimidine, particularly [1,2,4]triazolo[1,5-a]pyrimidine, pyridine, pyridazine and [4H,8H]-1,2,8-triazaindene. The compounds will have at least 12 atoms other than hydrogen, usually at least 15 atoms other than hydrogen, and not more than about 40, usually not more than 36, atoms other than hydrogen, where the atoms include carbon, chalcogen (O and S), halo, nitrogen and physiologically acceptable metal ions, generally Groups I and II of the Periodic Chart. Heteroatom containing substituents include oxy (hydroxyl and ether, where oxygen is bonded to hydrogen or an organic group) thio (thiol, thioether, sulfinic ester, sulfoxide, sulfone, sulfonic acid, sulfonic acid ester, sulfenamide, sulfonamide, etc., where sulfur is bonded to hydrogen, oxygen, nitrogen or an organic group), non-oxo-carbonyl (carboxylic acid, carboxylic acid salt, ester, and amide and the nitrogen, e.g. amidine, amic ester, N-oxy substituted, etc. and thio, e.g. thionocarboxylic acid, thiocarboxylic ester, etc., analogs thereof), oxo-carbonyl (aldehydo and keto), amino (I°, II°, III°, and IV° derivatives thereof, e.g. dialkylamino, carbamyl, amidinyl, N-oxy amidinyl, ureido, tetraalkylamino, etc.), halo (fluorine, chlorine, bromine, iodine and their anions), and the like. Groups substituted on the core heterocycle through a carbon atom include aliphatic, aliphatically saturated and unsaturated, generally having not more than 3 sites, usually not more than 2 sites, of unsaturation, alicyclic (included within aliphatic unless separately defined), carbocyclic aromatic of from 6–12, usually 6–10, annular members and heterocyclic of from 5 to 12, usually 5 to 10, annular members, and having from 1 to 4, usually 1 to 3 heteroannular members, usually chalcogen and nitrogen, where each of these rings may have from 0 to 4, usually 0 to 2 heteroatom containing substituents. The total number of carbon atoms will be in the range of about 9 to 20, usually 9 to 18, carbon atoms, while the number of heteroatoms will generally be in the range of about 3 to 12, more usually 4 to 10.

The four main core structures have the following formulas:

(1) triazolopyrimidines

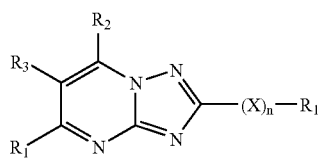

wherein the groups present are defined as follows:

X is a heteroatom linking group of from 1 to 7, usually 1 to 3 atoms other than hydrogen, including amino and substituted amino having an alkyl group of from 1 to 6, usually 1 to 2 carbon atoms, and usually unsubstituted, thio, sulfoxide and sulfone (sulfur having from 0–2 oxygen atoms), or oxy;

n is 0 or 1;

$R_1$ is hydrogen or an organic group of from 1 to 12, usually 1 to 10 carbon atoms and from 0 to 6, usually 0 to 4 heteroatoms, which are chalcogen, nitrogen, and halogen where the organic group may be aliphatic having from 0 to 4, usually 0 to 2 sites of unsaturation, e.g. alkyl, alkenyl and alkynyl, including alicyclic having from 0 to 2 sites of unsaturation, and includes alkyl of from 1 to 6 carbon atoms, usually 1 to 3, more usually 1 to 2, carbon atoms, non-oxocarbonyl and the nitrogen and sulfur derivatives thereof, particularly the nitrogen derivatives thereof, of from 3 to 12 atoms other than hydrogen, particularly 1 to 10 carbon atoms and 2 to 6, usually 2 to 4 heteroatoms, aryl, particularly phenyl, heterocyclic of from 3 to 6 annular members, and combinations thereof, e.g. aralkyl and alkaryl, where the cyclic structures may have from 1 to 3, commonly 1 to 2 rings, which may be fused or unfused, illustrated by methyl, ethyl, propyl, hexyl, phenyl, tolyl, fluorophenyl, anisole, phenetole, naphthyl, indolyl, quinolinyl, carboxy, ethoxycarbonyl, amidinyl, hydroxyamidinylmethyl, ethoxycarbamylethyl, phenylthioethyl, phenylaminopropyl, nitrophenethyl, p-nitrophenyl, mesitylethyl, 2-fluoro-5-ethylphenyl, 2,6-difluorophenyl, including the partial or completely reduced forms of the aromatic groups, e.g. pyridine and piperidine, etc., more particularly having a 6 membered aromatic group, particularly phenyl, having from 0 to 4, usually 0 to 3 substituents, which include alkyl of from 1 to 3 carbon atoms, particularly methyl, halo, particularly Cl and F, oxy of from 0 to 3 carbon atoms, trihalomethyl, cyano and nitro. $R_1$ may have an aryl group of from 6 to 10 carbon atoms, particularly phenyl, when X is nitrogen and n is 1.

$R_2$ is hydrogen, a heterofunctionality having nitrogen and/or chalcogen, which heterofunctionality is bonded to an annular carbon atom, where the heteroatom may be substituted with an organic group of from 1 to 10, usually 1 to 8 carbon atoms, and from 0 to 4, usually 0 to 3 heteroatoms, particularly alkyl of from 1 to 6, usually 1 to 2, carbon atoms, aryl, including alkaryl, aralkyl and aralkenyl of from 5 to 10 carbon atoms, aroyl of from 6 to 10 carbon atoms, or an organic group bonded through a carbon atom to the annular atom and of from 1 to 12, usually 1 to 8 carbon atoms, including aliphatic, alicyclic, aromatic and heterocyclic groups, having from 0 to 4, usually 1 to 2 heteroatoms, as described above for $R_1$;

$R_3$ is hydrogen or an organic group of from 1 to 10, usually 1 to 8 carbon atoms and from 0 to 4, usually 0 to 2 heteroatoms, usually chalcogen and nitrogen, particularly oxygen, including alkyl, oxycarbonyl, particularly alkoxycarbonyl, and aryl, alkaryl and aralkyl, particularly carbocyclic aryl, particularly of from 6 to 8 carbon atoms; and $R_4$ is hydrogen or alkyl and substituted alkyl of from 1 to 6, usually 1 to 3 carbon atoms, where the substituents are oxy, amino and halo, particularly fluoro; and where $R_3$ and $R_4$ may be taken together to form a ring with the atoms to which they are attached, having from 4 to 10, usually 4 to 8 annular atoms, which may be substituted or unsubstituted, particularly comprising a 1,4-butandiyl group having from 0 to 1 site of unsaturation to form a fused ring and adding from 1 to 2 rings, where the butandiyl may be fused to an additional ring so as to be a bicyclo substituent, wherein the annular atoms may be substituted with chalcogen, nitrogen, halo and alkyl of from 1 to 3 carbon atoms, particularly oxy of from 0 to 3 carbon atoms, thio of from 0 to 3 carbon atoms and amino of from 0 to 4 carbon atoms;

(2) di(arylthio)pyridines

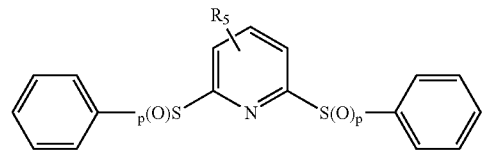

wherein:

p is 0, 1 or 2, usually 2; and $R_5$ is a group having from 1 to 3 atoms other than hydrogen and includes oxy, thio, amino, nitro, cyano, and alkyl, wherein $R_5$ is at the 3 or 4 position, usually the 3 position;

(3) aryl substituted pyridazinone (includes dihydropyridazine):

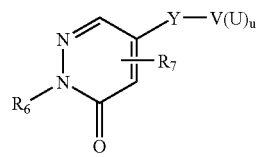

wherein:

Y is O, $S(O)_m$, wherein m is 0, 1 or 2, amino or $CH_2$;

$R_6$ is H or alkyl of from 1–3 carbon atoms;

$R_7$ is hydrogen, or a group of from 0 to 3 atoms other than hydrogen, and includes oxy, thio amino, nitro, cyano, and alkyl;

V is an aryl group having 6 annular members comprising 0 to 2 nitrogen atoms and the remainder carbon atoms U is a substituent group of from 0 to 5 atoms other than hydrogen, and includes oxy, thio amino, nitro, cyano, halo, and alkyl, usually of from 1 to 3 carbon atoms, while u is 0 to 3, usually 0 to 1;

(4) diazolohexahydroquinoline

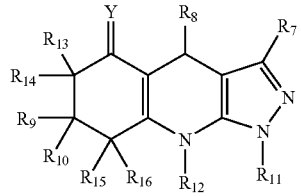

wherein:

Y is oxygen, sulfur, NH, (alkyl of from 1 to 3 carbon atoms, H) or $H_2$;

$R_7$ is hydrogen, a heterosubstituent of from 1 to 3 heteroatoms as described previously, or an organic group of from 1 to 12, usually 1 to 10, more usually 1 to 6 carbon atoms and from 0 to 6, usually 0 to 4 heteroatoms, which are chalcogen, nitrogen, and halogen where the organic group may be aliphatic having from 0 to 4. usually 0 to 2 sites of unsaturation, e.g. alkyl, alkenyl and alkynyl, including alicyclic having from 0 to 2 sites of unsaturation, and includes alkyl of from 1 to 6 carbon atoms, usually 1 to 3, more usually 1 to 2, carbon atoms, non-oxo-carbonyl and the nitrogen and sulfur derivatives thereof, particularly the nitrogen derivatives thereof, of from 3 to 12 atoms other than hydrogen, particularly 1 to 10 carbon atoms and 2 to 6, usually 2 to 4 heteroatoms, where the aliphatic groups may be substituted with from 1 to 4, usually 1 to 2 heterosusbtituents, which have been described above, aryl, particularly phenyl, heterocyclic of from 3 to 6 annular members, and combinations thereof, e.g. aralkyl and alkaryl, where the cyclic structures may have from 1 to 3, commonly 1 to 2 rings, which may be fused or unfused, illustrated by methyl, ethyl, propyl, hexyl, phenyl, tolyl, fluorophenyl, anisole, phenetole, naphthyl, furanyl, thienyl, indolyl, quinolinyl, carboxy, ethoxycarbonyl, amidinyl, hydroxyamidinylmethyl, ethoxycarbamylethyl, phenylthioethyl, phenylaminopropyl, nitrophenethyl, p-nitrophenyl, mesitylethyl, 2-fluoro-5-ethylphenyl, 2,6-difluorophenyl, including the partial or completely reduced forms of the aromatic groups, e.g. pyridine and piperidine, etc., more particularly having a 6 membered aromatic group, particularly phenyl, having from 0 to 4, usually 0 to 3 substitutents, which include alkyl of from 1 to 3 carbon atoms, particularly methyl, halo, particularly Cl and F, oxy of from 0 to 3 carbon atoms, trihalomethyl, cyano and nitro.

$R_8$ is hydrogen, a heterosubstituent of from 1 to 3 heteroatoms as described above, or an organic group of from 1 to 12, usually 1 to 10 carbon atoms, more usually 1 to 6 carbon atoms, and from 0 to 6, usually 0 to 4 heteroatoms, which are chalcogen, nitrogen, and halogen where the organic group may be aliphatic having from 0 to 4, usually 0 to 2 sites of unsaturation, e.g. alkyl, alkenyl and alkynyl, including alicyclic having from 0 to 2 sites of unsaturation, and includes alkyl of from 1 to 6 carbon atoms, usually 1 to 3, more usually 1 to 2, carbon atoms, non-oxo-carbonyl and the nitrogen and sulfur derivatives thereof, particularly the nitrogen derivatives thereof, of from 3 to 12 atoms other than hydrogen, particularly 1 to 10 carbon atoms and 2 to 6, usually 2 to 4 heteroatoms, aryl, particularly phenyl, heterocyclic of from 3 to 6 annular members, and combinations thereof, e.g. aralkyl and alkaryl, where the cyclic structures may have from 1 to 3, commonly 1 to 2 rings, which may be fused or unfused, or a heterosusbtituent of from 1 to 3 heteroatoms as described previously, illustrated by methyl, ethyl, propyl, hexyl, phenyl, tolyl, fluorophenyl, anisole, phenetole, naphthyl, indolyl, quinolinyl, carboxy, ethoxycarbonyl, amidinyl, hydroxyamidinylmethyl, ethoxycarbamylethyl, phenylthioethyl, phenylaminopropyl, nitrophenethyl, p-nitrophenyl, mesitylethyl, 2-fluoro-5-ethylphenyl, 2,6-difluorophenyl, including the partial or completely reduced forms of the aromatic groups, e.g. pyridine and piperidine, etc., more particularly having a 6 membered aromatic group, particularly phenyl, having from 0 to 4, usually 0 to 3 substitutents, which include alkyl of from 1 to 3 carbon atoms, particularly methyl, halo, particularly Cl and F, oxy of from 0 to 3 carbon atoms, trihalomethyl, cyano and nitro. More particularly, $R_8$ is hydrogen, alkyl of from 1 to 6, usually 1 to 3 carbon atoms or substituted alkyl, where the substituents have been described in relation to or a heterocycle of from 5 to 6 annular members and from 1 to 2 heteroannular members that are oxygen, nitrogen or sulfur, having a total number of atoms other than hydrogen in the range of 5 to 10, usually 5 to 8; and $R_9$, $R_{10}$, $R_{13}$, $R_{14}$, $R_{15}$ and $R_{16}$ are the same or different, usually not more than two, more usually not more than one, being other than H; when not H, the groups will come within the definition of $R_8$, generally being alkyl or substituted alkyl of from 1 to 6, usually 1 to 3 carbon atoms, having 0 to 2, usually 0 to 1 substituent as described above, a heterosusbtituent of from 1 to 3 heteroatoms that are chalcogen, nitrogen or halo, oxy, thio or amino of from 0 to 8, usually 0 to 6 carbon atoms, wherein aliphatic, aromatic and heterocyclic substituents may have in turn from 0 to 2 substituents as described above, particularly alkyl or substituted alkyl of from 1 to 4, usually 1 to 3 carbon atoms $R_{11}$ and $R_{12}$ are the same or different and are H or an organic group of from 1 to 12, usually 1 to 8, more usually 1 to 6 carbon atoms and 0 to 6, usually 0 to 4 heteroatoms that are chalcogen, nitrogen and halo, particularly aliphatic (including alicyclic) of from 1 to 8, usually 1 to 3 carbon atoms, substituted or unsubstituted, having from 0 to 3, usually 0 to 2, substituents as described above, aromatic of from 6 to 12, usually 6 to 10 carbon atoms, substituted or unsubstituted, having from 0 to 3, usually 0 to 2, substituents as described above, and heterocyclic having from 3 to 6 annular members with from 1 to 3 heteroatoms that are chalcogen and nitrogen; particularly hydrogen or alkyl of from 1 to 3 carbon atoms.

Of the four formulas, the core structure of the triazolopyrimidine is of particular interest. This family of compounds is recognized by having at the 2-position ($(X)_n$—$R_1$), where X is amino, thio or sulfone, n is 0 or 1, where the amino may be unsubstituted or substituted with lower alkyl of from 1 to 3 carbon atoms, and $R_1$ is a lower alkyl group of 1 to 3 carbon atoms, particularly methyl, or an organic group having a six annular membered aromatic group, particularly phenyl or pyridinyl group, preferably phenyl, having from 0 to 3 substituents, where the substituents are halo, particularly chloro, lower alkyl of from 1 to 3 carbon atoms, particularly methyl, nitro, trihalomethyl, particularly trifluoromethyl, and where the phenyl group is terminal and is either directly bonded to the amino or thio atom or bonded through a linking group of from 1 to 4, usually 1 to 3, atoms in the chain, being carbon, nitrogen, or chalcogen, particularly carbon and nitrogen, where heteroatoms are bonded solely to carbon and hydrogen, there being from 0 to 2 heteroatoms in the chain, the linking group generally being a total of from 1 to 8 atoms, usually 1 to 6 atoms other than hydrogen and having from 0 to 2 heterosusbtituents, e.g. oxo, or having α-acetamidinyl having from 0 to 1 N—OH, i.e. N-hydroxy α-acetamidinyl.

$R_2$ is a carbocyclic bonded to the annular carbon atom by a linking group of from 1 to 3 atoms having from 0 to 1 heteroatom that is chalcogen or nitrogen, particularly amino (—NH—), wherein the ring has from 3 to 6 annular atoms, particularly 3 to 4, a group of from 0 to 3 carbon atoms that is lower alkyl of from 1 to 3 carbon atoms, particularly methyl, oxy, or amino, phenyl or substituted phenyl bonded directly to an annular atom or through a carbamyl or vinyl group, where the substituents are oxy of from 0 to 3 carbon atoms, particularly alkoxy, more particularly methoxy, or lower alkyl of from 1 to 3 carbon atoms, particularly methyl, or a heterocycle of from 5 to 6 annular members, having from 1 to 2, usually 1, annular heteroatom, where the annular heteroatoms are chalcogen and nitrogen, and having from 0 to 1 substituent of from 0 to 3 carbon atoms. Illustrative groups include amino, ethylamino, dimethylamino, hydroxy, propyloxy, ethoxy, methoxy, phenyl, tolyl, mesityl, phenetole, anisole, chlorophenyl, bromotolyl, styryl, p-ethoxystyryl, phenethylamine, benzylamine, N-phenyl aminocarbonyl (—NHCO—), N-2,4-dichlorophenyl aminocarbonyl, N-anisolyl aminocarbonyl, pyridinylmethyl, thiophenyl, thiazolinyl and piperidinyl, as well as the groups described for $R_3$.

$R_3$ is hydrogen or an organic group of from 1 to 8 carbon atoms and 0 to 4, usually 0 to 3 heteroatoms, the heteroatoms being chalcogen, nitrogen and halo, being aliphatic, unsaturated or saturated, particularly saturated, including alkyl of from 1 to 6 carbon atoms and having 0 to 2, usually 0 to 1, site of aliphatic unsaturation, non-oxo carbonyl of from 1 to 4 carbon atoms, carbocyclic bonded to the annular carbon atom by a linking group of from 1 to 3 atoms having from 0 to 1 heteroatom that is chalcogen or nitrogen, particularly amino (—NH—), wherein the ring has from 3 to 6 annular atoms, particularly 3 to 4, and alkoxycarbonyl, where the alkoxy group is of from 1 to 3 carbon atoms. Illustrative groups include methyl, propyl, allyl, propargyl, 3-butenyl-1, cyclopropylethyl, cyclobutylmethyl, cyclopropylpropylamino, cyclopropylmethoxy, cyclopentyl, allylamino, hexoxy, butoxyformyl, phenyloxyformyl, and methoxyethylformyl.

$R_4$ is hydrogen, lower alkyl of from 1 to 3 carbon atoms, particularly methyl, alkoxyalkyl of from 2 to 5, usually 2 to 4 carbon atoms, or haloalkyl of from 1 to 3 carbon atoms and from 1 to 4 halo atoms, usually fluoro, more particularly trifluoromethyl, where $R_4$ is preferably hydrogen or lower alkyl of from 1 to 3 carbon atoms, particularly methyl. Illustrative groups include methyl, propyl, isobutyl, 4-methylpentyl, 3-chloropropyl, 4,4,4-trifluorobutyl, 2-fluoroethyl, trifluoromethyl, and 2,3-difluoropropyl.

In referring to aliphatic groups, the aliphatic groups will include alkyl groups that are branched or straight chain, generally having from 1 to 6, usually 1 to 3 carbon atoms, and having from 0 to 3 heteroatoms that are chalcogen, nitrogen and halogen, usually being oxy of from 0 to 3 carbon atoms, amino of from 0 to 4 carbon atoms, and thio having from 0 to 2 oxygen atoms and of from 0 to 3 carbon atoms, being saturated or unsaturated having from 0 to 3 sites of unsaturation, namely double and triple bonds.

In referring to aryl groups, both carbocyclic and heterocyclic groups are intended, particularly nitrogen heterocycles, where there will be from 5 to 12, usually 5 to 10, annular atoms, more particularly 5 or 6 annular atoms, and having from 0 to 8, usually 0 to 6, more frequently 0 to 3 heteroatoms, as chalcogen, nitrogen, and halo, and being substituted or unsubstituted, where the substituents will be of from 1 to 8, usually 1 to 6 atoms other than hydrogen, generally having from 0 to 6, usually 0 to 3 carbon atoms, and include oxy, thio, amino, non-oxo-carbonyl, including the nitrogen and sulfur analogs thereof, oxo-carbonyl, halo, cyano, nitro, etc.

In referring to heterocyclic groups, these groups will be generally non-aromatic and have from 5 to 10, usually 5 or 6 annular members, having from 1 to 3, usually 1 to 2, heteroatoms per ring, which are chalcogen and nitrogen, being saturated or unsaturated, generally having from 0 to 3, usually 0 to 2 sites, of ethylenic unsaturation, and being unsubstituted or substituted, having from 0 to 3 substituents.

Substituents will generally include alkyl of from 1 to 6, usually 1 to 3, carbon atoms, haloalkyl of from 1 to 3 carbon atoms and from 1 to 7, usually 1 to 5, halo atoms, particularly fluoro, halo, particularly Cl, oxy of from 0 to 3 carbon atoms, thio of from 0 to 8, particularly 6 to 8, carbon atoms having 0 to 2 oxygen atoms bonded to sulfur, amino of from 0 to 8 carbon atoms, usually when alkylamino of from 1 to 4 carbon atoms, when aryl amino of from 6 to 8 carbon atoms and when aroylamino of from 7 to 8 carbon atoms, nitro, cyano, halo, particularly fluorine and chlorine, and non-oxo-carbonyl of from 1 to 6, usually 1 to 3, carbon atoms, primarily acid and ester.

Of particular interest are the triazolopyrimidines. More particularly, are those compounds that modulate the activity of the EPO-R, where modulation intends that a detectable signal is transduced into the cell upon binding of the compound, e.g. expression of a protein. Compounds coming within this class are indicated using the designation of the above formula are as follows. These compounds will usually have X as S or NH. $R_1$ will usually be alkyl of from 1 to 3 carbon atoms, particularly $CH_3$, substituted phenyl bonded directly to an annular carbon atom or through a linking group of from 1 to 3 atoms in the chain having from 0 to 3, usually 1 to 2, the atoms being carbon and nitrogen, more particularly methylene and aminoethylene, and the phenyl group being unsubstituted or having substituents that are $CH_3$, Cl, $NO_2$, and $CF_3$,. $R_2$ is $CH_3$, $NH_2$, OH, and aroylamido of from 7 to 8 carbon atoms having from 0 to 2 susbtituents that are $CH_3$, Cl, $NO_2$, and $CF_3$, particularly toluoylamido. $R_3$ is cycloalkylalkyl of from 4 to 8, usually 4 to 6 carbon atoms, having from 3 to 4 annular atoms, H or carboxy. $R_4$ is H, lower alkyl of from 1 to 3 carbon atoms, particularly $CH_3$, or alkoxymethyl of from 2 to 4 carbon atoms, particularly methoxymethyl. $R_3$ and $R_4$ may be taken together to define phenyl-1,2-dimethylene-α-halo, α-$CH_3$, where the rings may be further susbtituted with from 1–2 substituents that are halo, e.g. F and Cl, $NO_2$, $CH_3$, and $CF_3$. ork, 1987.

When $R_3$ is an aliphatic group (aliphatic intends alkyl, cycloalkyl, and combinations thereof, whether aliphatically saturated or unsaturated), or an aliphatic group substituted amine of from 2 to 6, usually 3 to 5 carbon atoms, wherein cycloalkyl is of from 3 to 4 carbon atoms, generally saturated, X, n, $R_1$, $R_2$, and $R_4$, will have the following definitions. X is NH or S and n is 1. $R_1$ is alkyl of from 1 to 3 carbon atoms, particularly methyl, or phenyl having from 0 to 3 substituents, particularly 2 to 3 substituents that include $CH_3$, $CF_3$, $NO_2$, and Cl, linked to X directly or through a linking chain of from 2 to 4 atoms in the chain consisting of C and N, wherein N is bonded solely to carbon, and having from 0 to 1 non-oxo carbonyl group; $R_2$ is H, alkyl of from 1 to 3 carbon atoms, particularly $CH_3$, OH, $OCH_3$, and $NH_2$; and $R_4$ is H and $CH_3$. When $R_2$ has the aliphatic group, then the definition of $R_3$ will be substituted by the definition of $R_2$, with the other definitions remaining the same.

When $R_3$ is H, X, n, $R_1$, $R_2$ and $R_4$ will have the following definitions. X is NH or S and n is 1. $R_1$ is alkyl of from 1 to 3 carbon atoms, particularly methyl, or phenyl having from 0 to 3 substitutents, particularly 2 to 3 substituents that include $CH_3$, $CF_3$, $NO_2$, and Cl, with the phenyl group linked to X directly or through a linking chain of from 1 to 4 atoms in the chain consisting of C and N, wherein N is bonded solely to carbon, and having from 0 to 1 non-oxocarbonyl group, or amidinyl methyl having from 0 to 1 N-hydroxyl group; $R_2$ is H, alkyl of from 1 to 3 carbon atoms, particularly $CH_3$, OH, $OCH_3$ and $NH_2$ a heterocycle having 5 to 6 annular members, particularly 5, where the heteroatoms are chalcogen and nitrogen, particularly chalcogen and having from 0 to 2, usually 1 to 2, sites of unsaturation, or phenyl having from 0 to 2, usually 1–2 substituents, that are $CH_3$, Cl, $OCH_3$, and $NO_2$, where phenyl is bonded to the annular carbon atoms directly or through an aliphatic hydrocarbon chain of from 1 to 3, usually 1 to 2 carbon atoms, having from 0 to 1 site of ethylenic unsaturation; and $R_4$ is H and $CH_3$.

When $R_3$ comprises a non-oxo-carbonyl group (particularly acid, ester or amide) of from 1 to 5, usually 1 to 4, carbon atoms, particularly 1 or 3), wherein the oxo group is bonded directly to an annular atom, X, n, $R_1$, $R_2$ and $R_4$ will have the following definitions. X is NH or S and n is 1. $R_1$ is alkyl of from 1 to 3 carbon atoms, particularly $CH_3$, or phenyl having from 0 to 2 substituents that are $CH_3$, Cl, $NO_2$ or $OCH_3$, particularly methyl and phenyl is bonded directly to an annular atom or through a linking group of from 1 to 3 atoms in the chain, particularly carbon and nitrogen, usually $CH_2$; $R_2$ is $CH_3$, OH, $OCH_3$, or $NH_2$, particularly OH or $NH_2$; and $R_4$ is H or $CH_3$, particularly H.

When $R_3$ is phenyl having from 0 to 2 substituents and bonded directly to an annular atom or through a linking group of from 1 to 3 atoms in the chain which are carbon and nitrogen, particularly $CH_2$, where the substituents are $CH_3$, Cl, $NO_2$ and $OCH_3$, X, n, $R_1$, $R_2$ and $R_4$ will have the following definitions. X is NH or S and n is 1. $R_1$ is phenyl having from 0 to 3 substituents, usually 1 to 2 substituents that are $CH_3$, Cl, $NO_2$ and $OCH_3$, bonded directly or through $CH_2$ to an annular atom. $R_2$ is $CH_3$, OH, $OCH_3$, and $NH_2$, particularly OH and $OCH_3$. $R_4$ is H or $CH_3$.

Exemplary compounds that have been shown to be active in modulating EPO-R response to EPO are as follows:

The following compound has been designated as E5

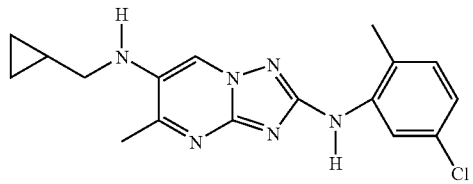

The following compound is designated as EM5:

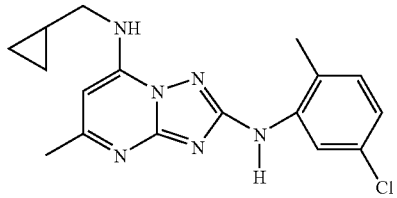

The triazolopyrimidines of the subject invention are referred to as the E5 (including EM5) family for convenience. The following table sets forth compounds that have been prepared and tested for binding to the modulating domain. All of the compounds set forth have specific affinity to the modulating domain with members of the group providing modulation of the EPO-R activity in transducing a signal into a cell.

TABLE 1

E5 Analog Non-peptide EPO-R Modulators

| Cmpnd | —(X)$_n$— | $R_1$ | $R_2$ | $R_3$ | $R_4$ |
|---|---|---|---|---|---|
| E5* | NH | (2-methyl-5-chlorophenyl) | H | (cyclopropylmethylamino) | $CH_3$ |
| E5-A20 | S | (amidinyl methyl with N-OH, NH$_2$) | $CH_3$ | H | $CH_3$ |
| E5-A24 | S | (—CO—HN—C$_6$H$_4$—Cl group) | $CH_3$ | H | $CH_3$ |

TABLE 1-continued

E5 Analog Non-peptide EPO-R Modulators

| Cmpnd | —(X)$_n$— | R$_1$ | R$_2$ | R$_3$ | R$_4$ |
|---|---|---|---|---|---|
| E5-A25 | S | *3,5-dichlorophenyl-NH-C(=O)-CH$_2$-* | CH$_3$ | H | CH$_3$ |
| E5-A14 | S | *4-chlorobenzyl* | CH$_3$ | H | CH$_3$ |
| E5-A2 | S | CH$_3$ | NH$_2$ | —COOH | H |
| E5-A9 | NH | *2-methyl-4-chlorophenyl* | OH | | *2-chloro-6-(1-fluoroethyl)benzyl* |
| E5-A16 | S | *2-nitrophenyl* | CH$_3$ | H | CH$_3$ |
| E5-A18 | S | *3-nitro-4-trifluoromethylphenyl* | CH$_3$ | H | CH$_3$ |
| E5-A4 | S | CH$_3$ | *3-methyl-benzamido-N-* | H | H |
| E5-A10 | NH | *4-chloro-2-methylphenyl* | OH | H | —CH$_2$—O—CH$_3$ |

*R$_2$ and R$_3$ when switched also provide an active compound.

TABLE 2

E5 Analog Non-peptide EPO-R Non-modulating Binding Molecules

| Cmpnd | —(X)$_n$— | R$_1$ | R$_2$ | R$_3$ | R$_4$ |
|---|---|---|---|---|---|
| E5-A1 | S | CH$_3$ | NH$_2$ | *ethyl-O-C(=O)-* | H |
| E5-A3 | S | CH$_3$ | NH$_2$ | H | H |

TABLE 2-continued
E5 Analog Non-peptide EPO-R Non-modulating Binding Molecules
| Cmpnd | —(X)$_n$— | R$_1$ | R$_2$ | R$_3$ | R$_4$ |
|---|---|---|---|---|---|
| E5-A5 | S | CH$_3$ | OCH$_3$ | H | CH$_3$ |
| E5-A6 | —SO$_2$— | CH$_3$ | OCH$_3$ | H | CH$_3$ |
| E5-A7 | n = 0 | H | OH | H | CH$_3$ |
| E5-A8 | S | CH$_3$ | OH | H | CH$_3$ |
| E5-A11 | NH | 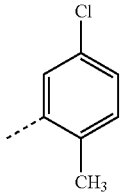 | OH | 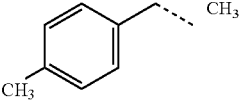 | CH$_3$ |
| E5-A12 | S | H | CH$_3$ | H | CH$_3$ |
| E5-A13 | S | CH$_3$ | CH$_3$ | H | CH$_3$ |
| E5-A15 | S |  | OH | H | CH$_3$ |
| E5-A17 | S | 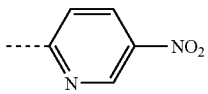 | CH$_3$ | H | CH$_3$ |
| E5-A19 | S | 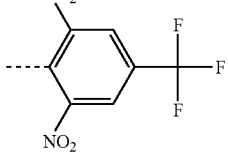 | CH$_3$ | H | CH$_3$ |
| E5-A21 | n = 0 | H | 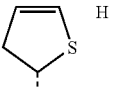 | H |  |
| E5-A22 | S | 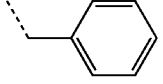 | OH | 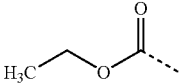 | H |
| E5-A23 | S |  | OH | 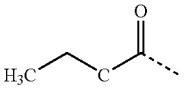 | H |
| E5-A28 | NH | H | 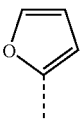 | H | H |
| E5-A30 | NH | H | 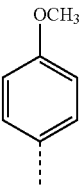 | H | H |

TABLE 2-continued

E5 Analog Non-peptide EPO-R Non-modulating Binding Molecules

| Cmpnd | —(X)$_n$— | R$_1$ | R$_2$ | R$_3$ | R$_4$ |
|---|---|---|---|---|---|
| E5-A31 | NH | H | OCH$_3$ | H | H |

For the aryl substituted pyridazinones, the following are preferred.

X is thio, particulary sulfone, y is 0 to 1, and

R$_7$ is H, halo, particularly Cl, alkyl of from 1 to 3 carbon atoms, particularly methyl, OH or OCH$_3$.

The following compound is designated as E6.

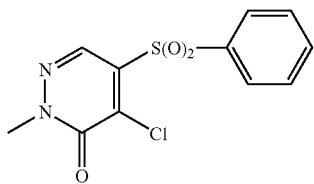

The following compound is designated as E4.

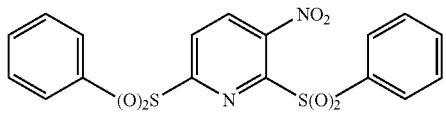

For the diazolohexahydroquinolines, the following are preferred:

R$_7$, R$_{9-10}$ and R$_{13-16}$ are the same or different, at least 2 and not more than 4 being other than H, and are otherwise alkyl or substituted alkyl of from 1 to 6, usually 1 to 3 carbon atoms and from 0 to 1 substituent, particularly chalcogen and amino, where the heteroatom may be bonded to the annular atom, heterocyclic of from 3 to 6 annular atoms, having from 1 to 2 annular heteroatoms that are chalcogen or nitrogen, and aromatic of from 6 to 8 carbon atoms having from 0 to 2 substituents including alkyl, oxy and halo;

R$_8$ is H, an organic group of from 1 to 12, usually 1 to 6 carbon atoms or a heterosubstituent of 1 to 3 heteroatoms as described above, where the organic group may be bonded directly to the annular carbon atom or through a heteroatom that is chalcogen or nitrogen, the organic group can be aliphatic (including alicyclic) of from 1 to 12, usually 1 to 6, more usually 1 to 3 carbon atoms, which group may be substituted with substituents as indicated previously, aromatic of from 6 to 10, usually 6 to 8 carbon atoms, or heterocyclic of from 3 to 6 annular members, particularly 5 to 6 annular members having from 1 to 3, usually 1 to 2 heteroatoms that are chalcogen and nitrogen and may be saturated or unsaturated, and combinations thereof Exemplary groups include methyl, methoxyethyl, cyanoethyl, acetyl, N-methyl carbamyl, trifluoromethyl, cyclopropylmethyl, chlorophenyl, phenetole, pyranyl, furanyl, thiophenyl, pyrrolyl, piperidinyl, pyridinyl, methylpyridinyl, etc.

R$_{11}$ and R$_{12}$ may be the same or different and include H, an organic group of from 1 to 12, usually 1 to 6 carbon atoms, particularly aliphatic (including alicyclic), particularly alkyl or acyl, which group may be substituted with substituents as indicated previously, aromatic of from 6 to 10, usually 6 to 8 carbon atoms, or heterocyclic of from 3 to 6 annular members, particularly 5 to 6 annular members having from 1 to 3, usually 1 to 2 heteroatoms that are chalcogen and nitrogen and may be saturated or unsaturated, and combinations thereof. Illustrative substituents include methyl, ethyl, hydroxyethyl, glycolyl, acetyl, butyryl, cyclobutylmethyl, chlorophenyl, tolyl, pyranyl, furanyl, pyrrolyl, pyrrolidinyl, piperidinyl, pyridinyl, pyrazinyl, etc.

The following compound is of particular interest and is designated E5A29

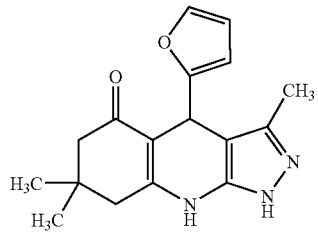

The subject compounds may be provided in a variety of ways, particularly in combination with other materials, both active and inactive for the purpose intended for the subject compounds. The subject compounds may be provided as the only active ingredient or may be provided as a complex with at least the modulation domain of the EPO-R. In the former situation, the subject compounds will usually be provided with a variety of diluents to allow for use at low concentrations, e.g. drug formulation or assay reagent. Alternatively, the subject compounds may be prepared as complexes with at least the modulating domain of the EPO-R so as to be used in assays for competitive binding, where release of the subject compound is to be determined. The subject compound may be provided together with at least the modulating domain of the EPO-R in separate containers or in a single container as a dry or liquid formulation, complexed or uncomplexed or both.

The subject compounds find many applications associated with the EPO-R and EPO. The subject compounds can be used in affinity columns where one or more of the subject compounds may be functionalized and bonded to packings for affinity columns. Packings for affinity columns include Agarose, Sepharose, Sephadex, Latex, etc. Numerous literature references describe methods of functionalizing compounds and linking them to active or activated particles. Also, one may functionalize gels for electrophoresis, where the EPO-R will complex with the subject compounds with a reduction in its migratory rate. See, for example, U.S. Pat. Nos. 5,445,958; 6,033,574; 6,258,275; 6,281,006, and references cited therein.

The subject compounds may also be used to count the number of EPO-R present. Particularly, one may evaluate the effect of changes in the environment of cells on the up or down regulation of EPO-R as observed with the EPO-R population at the cellular membrane. By having the subject compounds labeled with a detectable label, e.g. radioisotope, fluorescer, etc., after contacting the cells with the labeled derivative of the subject compounds, one washes away non-specifically bound labeled derivative and then measures the amount of labeled derivative still bound to the cells. By employing a standard, where one knows the EPO-R population in a predetermined environment, one can determine whether the change in environment affects the surface EPO-R population. Changes in environment may be test compounds for the ability to modulate the EPO-R population by binding to the ligand site or modulating the expression of EPO-R. The subject compounds may also be used to isolate cells expressing the EPO-R receptor. By binding the subject compounds to a surface, e.g. container wall, beads, particularly, magnetic beads, capillary wall, etc., one can disperse cells in an appropriate medium and contact the dispersed cells with the bound subject compounds. After washing away non-specifically bound cells, one can isolate cells expressing EPO-R and transporting the EPO-R to the cell membrane.

The subject compounds can be used for competitive assays for determining whether other compounds bind to the modulating domain. By using labeled derivatives of the subject compound to compete with test compounds, one can evaluate the binding affinity of the test compound. By combining a labeled subject compound and a test compound with EPO-R under complex forming conditions, the amount of labeled subject compound bound to the EPO-R will be related to the affinity of the test compound. Various assay protocols are known for competitive assays, for example, immobilizing the EPO-R and measuring the amount of the labeled derivative that binds to the immobilized EPO-R in the presence and absence of the test compound. With a fluorescer labeled subject compound, one may use total internal reflection to detect fluorescer adjacent the wall of the container. Alternatively, one may have a biotinylated subject compound. After combining the biotinylated subject compound, the test compound and EPO-R under complex forming conditions, one may separate the complex of the biotinylated subject compound and EPO-R using immobilized strept/avidin. After washing to remove any non-specifically bound EPO-R, one can add an enzyme labeled anti-(EPO-R) and measure the turnover rate of substrate of the enzyme. The turnover rate will be related to the affinity of the test compound for the modulating domain. Another method is to use the labeled subject compound as a complex with at least the modulating domain of the EPO-R and immobilize the complex. One can then determine the rate at which the labeled subject compound is released from the complex in the presence and absence of a test compound, indicating the affinity of the test compound.

Various labels find use in assays, such as radioisotopes, e.g. tritium, fluorescers, chemiluminescers, enzymes, quantum dots, etc. Alternatively, one may use uncommon isotopes and detect the compound by mass spectroscopy. The manner in which these various labels are incorporated into the subject compounds is well known by analogy. For example, methyl groups may be functionalized with a thiol group, whereby a maleimide-functionalized fluorescer can be attached through a thioether group. The acid group of an ester or amide may be replaced with an acid group of a chemiluminescer. Enzyme functionalized antibodies can be employed, where the antibody binds to the EPO-R complex with the subject compound.

The subject compounds form complexes with the extracellular portion of EPO-R. The complex is readily formed by bringing together a subject compound and at least the modulating domain portion of EPO-R under buffered conditions, having a pH usually in the range of about 5 to 10, more usually 6 to 9, including physiological conditions. Various buffers may be employed, e.g. tris, phosphate, borate, carbonate, MOPS, etc., generally at a concentration in the range of about 10 to 200 mM. The concentrations of the two components will depend upon the circumstances under which they are brought together, e.g. a synthetic mixture in an aqueous buffered medium, cells in a culture medium expressing EPO-R, administration to a host, etc. The concentration may range from 0.1 nM to saturation or greater. The EPO-R may be a purified molecule, a member of a lysate, a member of a mixture of proteins, present in a microsome, or present in a cell membrane, where the cell may be erythrocytic or other cell, may be a cell transformed with an EPO-R expression construct for expression of EPO-R under inducible or constitutive conditions, or the like. The complex may be a purified complex or may be present in a mixture as described above. The EPO-R may or may not have a ligand, e.g. EPO or mimetic, present in the ligand binding site of the complex.

Compounds that have physiological effect can be used in conjunction with a ligand for EPO-R, e.g. erythropoietin. In the presence of EPO, the non-peptide EPO-R modulators have an effect with EPO in activating EPO-R and transducing a signal into the cell, where less EPO can be used to obtain the same cellular response in the presence of a subject compound. For example, when added individually, very low concentrations of EPO and non-peptide EPO-R modulator give no or a very low number of CFU-e from bone marrow; whereas, when added together they give a maximum response.

The non-peptide EPO-R modulator can be administered to a subject (e.g., mammal) in vivo or to mammalian cells ex vivo or in vitro.

Enhancement of the cellular response to EPO by the non-peptide EPO-R modulators provides a means of improving the response of subjects that are either partially unresponsive, e.g. resistant, to the action of EPO or have low natural EPO levels. This is particularly desirable in some situations where the administration of EPO may have undesirable side effects or the host has diminished amounts of EPO.

In one method of use, non-peptide EPO-R modulators may be administered to subjects requiring enhancement of the response to naturally occurring levels of EPO. In an alternative method, the non-peptide EPO-R modulators may be administered to subjects in conjunction with EPO. In another alternative method, the non-peptide EPO-R modulators may be administered to patients with diminished amounts of EPO.

Non-peptide EPO-R modulators may be administered alone or together with exogenous EPO, in which case the administration can be simultaneous or sequential, as will be appreciated by those in the art. EPO is usually administered by injection, whereas the non-peptide EPO-R modulators may be administered by a variety of routes as described below.

The non-peptide EPO-R modulators may serve as EPO enhancers in a mammal. In addition, because of the effect between non-peptide EPO-R modulators and EPO, the non-peptide EPO-R modulators may also be used for enhancing the physiological effect of EPO binding to EPO-R by administration of non-peptide EPO-R modulators. Non-peptide EPO-R modulators may be used in methods for the diagnosis and therapy of diseases that involve inadequate or inappropriate EPO-R response.

Because the non-peptide EPO-R modulators may be used to replace or enhance the effect of EPO, the non-peptide EPO-R modulators may be used to treat diseases caused by an insufficient amount of EPO or by a lack of sufficient response to EPO, including hypoplastic anemia.

Anemia develops whenever there is a deficiency in erythrocyte count. It develops in response to various causes such as sickling disorders, homozygous beta thalassemia, hereditary spherocytosis, red cell enzymopathies, iron, vitamin $B_{12}$, folates deficiencies, aplastic anemia, Fanconi's anemia, Blackfan Diamond anemia, or leukemia. When a patient suffers from acute renal failure or when chronic renal failure develops, the inadequate renal production of erythropoietin results in hypoplastic anemia. Similarly, anemia in premature infants develops when a progressive fall in hemoglobin concentration, relatively low absolute reticulocyte counts, and bone marrow erythroid hypoplasia develops from low concentration of serum erythropoietin. Patients undergoing kidney dialysis frequently develop anemia.

The effect of reduced erythropoietin on development of anemia during chronic renal failure has been known and is further substantiated by findings described in Lancet, 1175 (1986) and in N.Engl.J.Med, 316: 731 (1987), which report that anemia in patients undergoing hemodialysis is completely reversed with recombinant human erythropoietin. These findings suggest that the anemia is due at least in part to erythropoietin deficiency.

As used herein, "treatment" is an approach for obtaining beneficial or desired results, including and preferably clinical results. Treatment can involve optionally either the amelioration of symptoms of a disease or condition, the prevention of symptoms of the disease or condition, or the delaying of the progression of the disease or condition. Diseases and conditions that may be treated using the non-peptide EPO-R modulators described in this application include but are not limited to the diseases and conditions described in this application (e.g., includes any disease or condition ameliorated or partially ameliorated by an increase in red blood cell level).

Because the subject compounds are not subject to rapid degradation upon administering orally or parenterally, a wide variety of formulations may be employed. Pharmaceutical compositions comprising a non-peptide EPO-R modulator and a pharmaceutically acceptable carrier, diluent, or excipient are provided. It will be appreciated the pharmaceutical composition may optionally include one or more additional components. In this application, unless the context makes clear otherwise, we refer to carriers, diluents, and excipients collectively as "excipients."

Generally, a pharmaceutical composition will include a therapeutically effective amount of a non-peptide EPO-R modulator and a pharmaceutically acceptable excipient. The pharmaceutical composition comprising a non-peptide EPO-R modulator may be provided in a unit dosage form.

In this application, by "pharmaceutically acceptable" means that the carrier, diluent or excipient is compatible with the other ingredients of the formulation and not deleterious to the recipient thereof. Pharmaceutically acceptable excipients are well known in the art and include sterile water for pharmaceutical use, isotonic solutions such as saline and phosphate buffered saline, physiological saline, and dextrose solution. In addition, the pharmaceutical composition or formulation can include other carriers, adjuvants, or non-toxic, non-therapeutic, non-immunogenic stabilizers, excipients and the like. The compositions can also include additional substances to approximate physiological conditions, such as pH adjusting and buffering agents, toxicity adjusting agents, wetting agents and detergents. Other excipients suitable for administration to a human patient are known in the art. See, e.g., *Remington: The Science and Practice of Pharmacy* (20th edition, 2000, Gennavo, ed.). The excipient is selected so as not to affect the biological activity of the agent or combination.

Depending upon the manner of administration of the non-peptide EPO-R modulators, the pharmaceutical compositions for delivery of the non-peptide EPO-R modulators may be formulated in a variety of ways.

The pharmaceutical compositions can be prepared in various forms, such as granules, tablets, pills, suppositories, capsules, suspensions, salves, lotions and the like. Pharmaceutical grade organic or inorganic carriers and/or diluents suitable for oral and topical use can be used to make up compositions containing the therapeutically-active compounds. Diluents known to the art include aqueous media, vegetable and animal oils and fats. Stabilizing agents, wetting and emulsifying agents, salts for varying the osmotic pressure or buffers for securing an adequate pH value, and skin penetration enhancers can be used as auxiliary agents.

The components used to formulate the pharmaceutical compositions are of high purity and are substantially free of potentially harmful contaminants (e.g., at least National Food (NF) grade, generally at least analytical grade, and more typically at least pharmaceutical grade). For human consumption, the composition is manufactured or formulated under GMP standards. For example, suitable formulations may be sterile and/or substantially isotonic and/or in full compliance with all Good Manufacturing Practice (GMP) regulations of the U.S. Food and Drug Administration.

In one version, the pharmaceutical composition comprises a non-peptide EPO-R modulator and a pharmaceutically acceptable carrier, where the non-peptide EPO-R modulator is selected from non-peptide EPO-R modulators described in this application. The subject compounds are normally uniformly distributed in the pharmaceutical composition, are in a form that is physiologically available to the host, in being transported to the site(s) for treatment, and are at concentrations to provide an effective dosage based on the manner of administration and the frequency of application or ingestion.

For therapy, the non-peptide EPO-R modulators may be administered by any means capable of delivering an effective amount of the non-peptide EPO-R modulator. Non-limiting examples of administration of the non-peptide EPO-R modulators include oral, topical, or parenteral administration, e.g. by injection at a particular site, for example, subcutaneously, intraperitoneally, intravascularly, intranasally, transdermally or the like. Formulations for injection will comprise a physiologically acceptable medium, such as water, saline, PBS, aqueous ethanol, aqueous ethylene glycols, or the like. Water soluble preservatives which may be employed include sodium bisulfite, sodium thiosulfate, ascorbate, benzalkonium chloride, chlorobutanol, thimerosal, phenylmercuric borate, parabens, benzyl alcohol and phenylethanol. Suitable water soluble buffering agents that may be employed are alkali or alkaline earth carbonates, phosphates, bicarbonates, citrates, borates, acetates, succinates and the like, such as sodium phosphate, citrate, borate, acetate, bicarbonate and carbonate. Additives such as carboxymethylcellulose may be used as a carrier. The formulation will vary depending upon the purpose of the formulation, the particular mode employed for modulating the receptor activity, the intended treatment, and the like. The formulation may involve patches, capsules, liposomes, time delayed coatings, pills, or may be formulated in pumps for continuous administration. The specific dosage can be determined empirically in accordance with known ways. See, for example Harrison's, Principles of Internal Medicine, 11th ed. Braunwald et al. ed, McGraw Hill Book Co., New York, 1987.

Generally, an "effective amount" or a "therapeutically effective amount" of a substance is that amount sufficient to effect a desired biological effect, such as beneficial results, including clinical results, and, as such, an "effective amount" depends upon the context in which it is being applied. In the context of administering a non-peptide EPO-R modulator to a vertebrate, human or other animal, a therapeutically effective amount may be an amount that can increase hematocrit levels in an animal (for example, an anemic human patient or other animal), e.g., an increase of at least about 10%, at least about 20%, at least about 50%, and may be about 100%, or more. Alternatively, an effective amount may be an amount of non-peptide EPO-R modulator sufficient to enhance the action of EPO in the human or non-human animal. For example, for a patient in need of administration of exogenous EPO (e.g., a patient with anemia) administration of an effective amount of non-peptide EPO-R modulator will be able to reduce the amount of exogenous EPO required to achieve a given endpoint (e.g., a designated level of erythrocytes in the animal, e.g., a normal or healthy level). The reduction in the amount of exogenous EPO employed, as compared to the absence of a subject compound, may be at least about 10%, often at least about 20%, sometimes at least about 50%, or more. An effective amount can be administered in one or more administrations in accordance with a predetermined regimen.

The amount of non-peptide EPO-R modulators given to each subject depends on pharmacological properties such as bioavailability, clearance rate and route of administration. The dosage will also depend upon the biological activity of the subject compound, the amount of EPO and/or other drugs being administered, the physiological condition of the host, and the like. Useful dosage ranges will be 0.01 to 200 µg/kg, more usually 0.05 to 100 µg/kg. Administration may be weekly or biweekly, or as often as daily, twice daily, more than twice daily, every two days, or less or more frequently, depending on the level of drug administered.

The host may be any mammal including domestic animals, pets, laboratory animals and primates, particularly humans. The amount will generally be adjusted depending upon the half life of the non-peptide EPO-R modulator, where dosages in the lower portion of the range may be employed where the non-peptide EPO-R modulator has an enhanced half life or is provided as a depot, such as a slow release composition comprising particles, introduced in a matrix which maintains the non-peptide EPO-R modulator over an extended period of time, e.g., a collagen matrix, use of a pump which continuously infuses the peptide over an extended period of time over a substantially continuous rate, or the like. Heller, *Biodegradable Polymers in Controlled Drug Delivery*, in: CRC Critical Reviews in Therapeutic Drua Carrier Systems, Vol. 1, CRC Press, Boca Raton, Fla., 1987, pp 39–90, describes encapsulation for controlled drug delivery, and Di Colo (1992) *Biomaterials* 13:850–856 describes controlled drug release from hydrophobic polymers.

The subject compounds are commercially available or may be readily synthesized by common synthetic strategies.

The E5 and E5 analog molecules described above are available from Maybridge, Plc (Cornwall, UK) and Key Organics Ltd (Cornwall, UK).

E5 may be synthesized as follows. There is literature precedent described (J. Het. Chem., (1999), 36, 183–188), which is summarized in Scheme 1, that will provide the core nucleus.

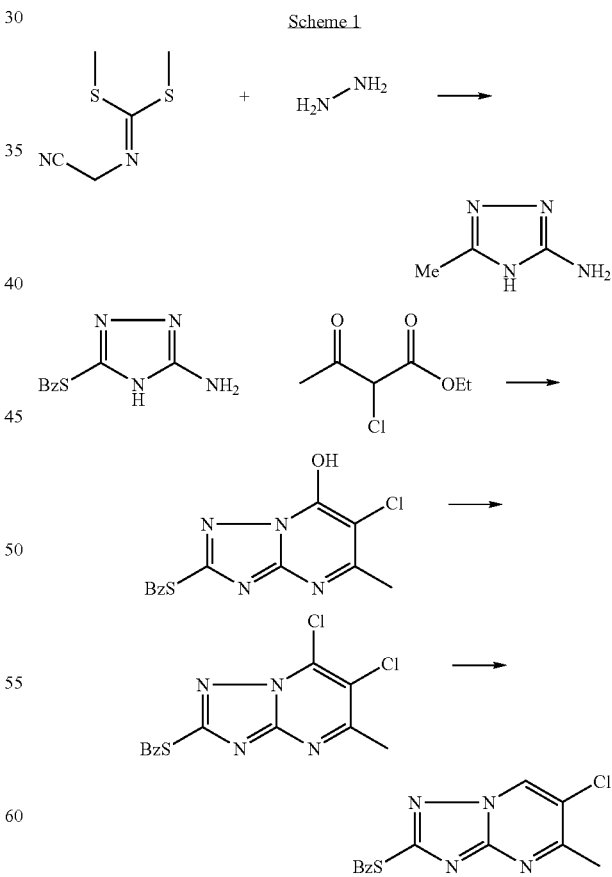

Scheme 1

The following route (scheme 2) may then be used to synthesize the E5 target molecule.

Scheme 2

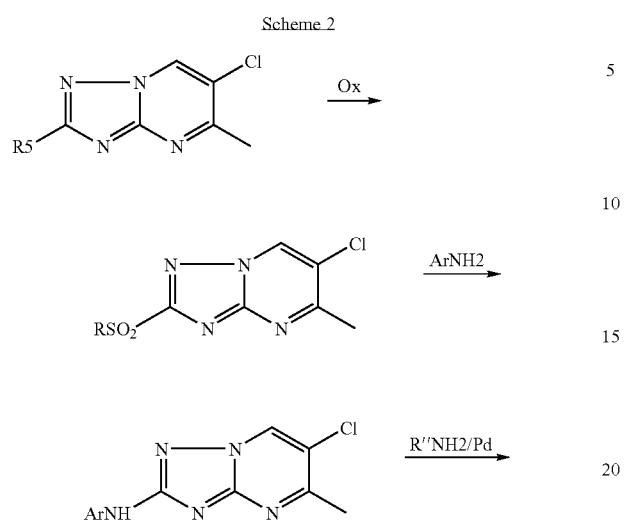

The E4 molecule described above is available from one of Maybridge, Plc (Cornwall, UK) and Key Organics Ltd (Cornwall, UK). The compound has been reported (London et al, J. Chem. Soc., (1939) 902–906, and Miller et al., Synth. Comm., (1978) 371–376) and there is precedent for the route of choice (Hamed et al, J. Chem. Soc., Perkin 1, (1997) 2415–2422); the starting materials are commercial available and the method of synthesis is shown in scheme 2 below.

Scheme 2

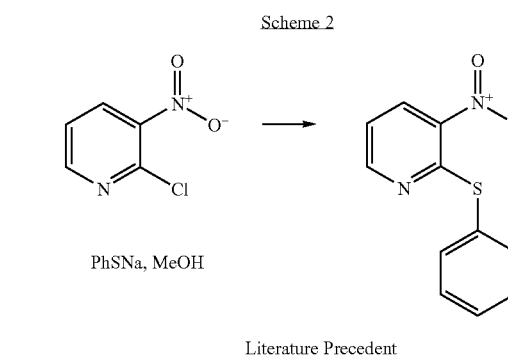

Literature Precedent

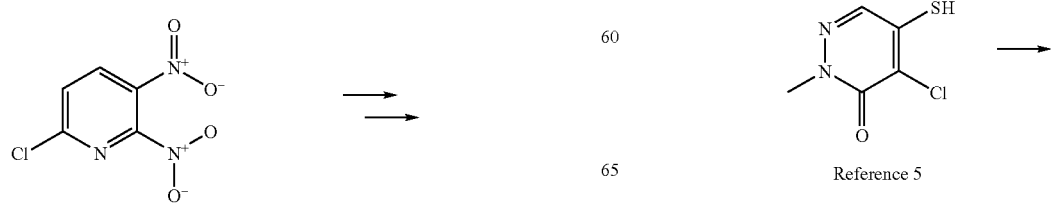

i PhSNa
ii AcOH, H₂O₂

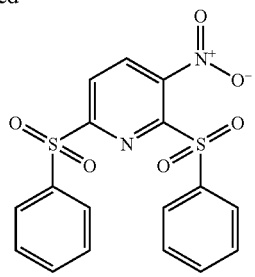

Aldrich

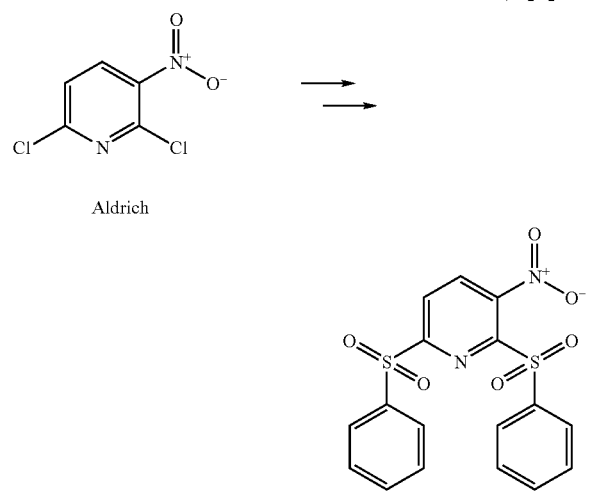

Proposed Route

The E6 molecule described above is available from one of Maybridge, Plc (Cornwall, UK) or Key Organics Ltd (Cornwall, UK).

E6 may be synthesized as follows:

The precursor compound has been reported (Kaji et al., Chem. Pharm. Bull., (1970), 18, 147–156) and the synthesis uses commercially available starting material, as shown in scheme 3.

Scheme 3

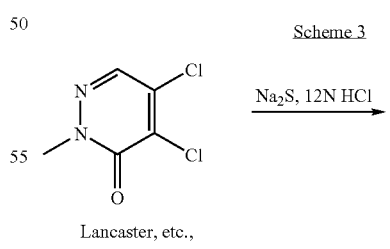

Reference 5

-continued

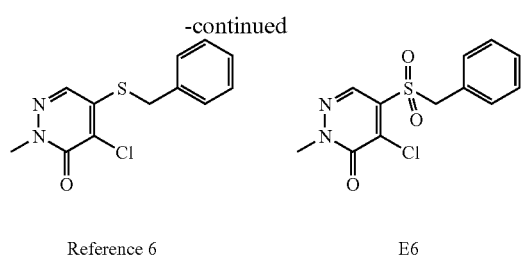

Reference 6
E6

Ref. 5. Kaji, et al., 1970 Chem Pharm Bull18, 147–56

Ref. 6. Latti, et al., 1998 J Labelled Compounds Radiopharm 41, 191–200

Generally, synthesis of analogs of E4, E5 and E6 may be accomplished using techniques of synthetic organic chemistry known to those in the art.

The compounds of the subject invention were shown to be active in binding to EPO-R and in some instances activating EPO-R in culture and in vivo. The initial competitive ERP screening assay was designed as a solid plate-binding assay. A detailed protocol of the assay is described below in the *Protocol for ERP Screen* section.

Briefly, in the competitive ERP screening assay, the extracellular portion of EPO-R was purchased from R&D (Minneapolis, Minn.); biotinylated and regular peptide were synthesized by American Peptide Company; receptor and biotinylated peptide (bio-ERP) were incubated at room temperature; the solution was contacted with neutravidin (streptavidin) coated plate to bind any complex between receptor and peptide; the complex that was bound to the plate is detected by antibody specific for EPO-R and detection is performed with HRP-conjugated secondary antibody; the presence of the complex between receptor and peptide is detected by light absorbance at 490 nm; and lack of or low signal indicates that the biotinylated peptide has been competed out, indicating an affinity of the test compound for the modulating domain of the EPO-R.

The library of compounds screened was created as a combination of two libraries: compounds were purchased from Maybridge Plc (Cornwall, UK) and Key Organics Ltd (Cornwall, UK). The libraries were received as microtiter plates. From the plates the compounds were diluted to 10 µM final concentration and used in a screen. Positive hits were identified as those compounds that were able to compete out the biotinylated-ERP peptide in its binding to the target site on EPO-R. 80% of competition was use as a cut off criteria for positive binders. Hits were retested in the binding assay to determine their dose-response curves.

Compounds identified in the initial screen were further tested for their biological activity in two assays: a cell proliferation assay and a cell signaling assay in TF-1 and UT-7 cells. The hit rate in cell proliferation was 0.16%; hit rate in cell signaling was 0.25%.

At the end of the biological testing in cell lines TF-1 and UT-7, E4, E5, E5 analogs and E6 molecules were some of the compounds identified as showing the best activity. The activity was compared to EPO natural hormone and it was observed that E4, E5, E5 analogs, and E6 molecules possess a maximum activity comparable to that of the maximum activity of EPO in the presence of low levels of EPO.

In addition to the above assays, further in vivo studies were undertaken (described in more detail below) including a Carboplatin induced anemia model, in which E4, E5, E5 analog, and E6 molecules were found to restore hematocrit levels in animals treated with carboplatin; and erythroid colony formation (CFU-e) experiments with mouse and human bone marrow, in which E4, E5, E5 analog, and E6 molecules were found to stimulate CFU-e formation to the same extent as EPO stimulates CFU-e formation.

The results of some of these assays are included in the figures of this application.

The subject compounds can be provided as kits, particularly for marketing, comprising at least a subject compound and instructions for its use. The instructions may be written or electronic, using various electronic media, such as CD, floppies, tapes, etc. for the instructions. The instructions may be labels provided with a therapeutic formulation, indicating dosages, side effects, acceptable and unacceptable combinations, and the like. For assays, the kits may include at least the modulating domain of EPO-R, a labeled subject compound, cells comprising EPO-R or cells able to upregulate the expression of EPO-R, and appropriate instructions as indicated above.

The following examples are intended to illustrate but not limit the invention.

Experimental

The initial competitive ERP screening assay was designed as a solid plate binding assay. A detailed protocol of the assay is described below in the *Protocol for ERP Screen* section.

Briefly, in the competitive ERP screening assay, the extracellular portion of EPO-R was purchased from R&D (Minneapolis, Minn.); biotinylated and regular peptide were synthesized by American Peptide Company; receptor and biotinylated peptide (bio-ERP) were incubated at room temperature; the solution was contacated with neutravidin (streptavidin) coated plate to bind any complex between receptor and peptide; the complex that was bound to the plate is detected by antibody specific for EPO-R and detection is performed with HRP-conjugated secondary antibody; the presence of the complex between receptor and peptide is detected by an light absorbance at 490 nm; and lack of or low signal indicates that the biotinylated peptide has been competed out, indicating an affinity of the test compound for the modulating domain of the EPO-R.

The library of compounds screened was created as a combination of two libraries: compounds were purchased from Maybridge Plc (Cornwall, UK) and Key Organics Ltd (Cornwall, UK). The libraries were received as microtiter plates. From the plates the compounds were diluted to 10 µM final concentration and used in a screen. Positive hits were identified as those compounds that were able to compete out the biotinylated-ERP peptide in its binding to the target site on EPO-R. 80% of competition was use as a cut off criteria for positive binders. Hits were retested in the binding assay to determine their dose-response curves.

Compounds identified in the initial screen were further tested for their biological activity in two assays: a cell proliferation assay and a cell signaling assay in TF-1 cells. The hit rate in cell proliferation was 0.16%; hit rate in cell signaling was 0.25%.

At the end of the biological testing in cell line, E4, E5, E5 analog, and E6 molecules were some of the compounds identified as showing the best activity. The activity was compared to EPO natural hormone and it was observed that E4, E5, E5 analog, and E6 molecules possess a maximum activity comparable to that of the maximum activity of EPO.

In addition to the above assays, further in vivo studies were undertaken (described in more detail below) including a Carboplatin induced anemia model, in which E4, E5, E5 analog, and E6 molecules were found to restore hematocrit levels in animals treated with carboplatin; and erythroid colony formation (CFU-e) experiments with mouse and human bone marrow, in which E4, E5, E5 analog, and E6 molecules were found to stimulate CFU-e formation to the same extent as EPO stimulates CFU-e formation.

The results of some of these assays are included in the figures of this application.

Protocol for ERP Screen

Candidate molecules were screened for EPO-R binding. Compounds were diluted in minisorb plates 1:20. 10 µl of the compound solution was added with matrix impact electronic multi pipettor into each well of the plate. 10 µl of cold peptide (with 5% DMSO) was then added (or HBS incl. 5% DMSO to control wells). ERP was diluted 1:4 (25 µl 1 mM+75 µL HBS, 250 µM) and put on ice. 26 µl of a 2 µM solution of EPO receptor was added to a receptor tube containing 2054 µl of HBS and vortexed a little. 20 µl of this solution was added to each well with repeat pipettor per well (10 nM in competition); 8.8 µl of a 250 µM solution of ERP-Biotin was added per tube with 2.2 ml HBS, and vortexed a little. 20 µl of this solution was dispensed with repeat pipettor into wells (400 nM in competition). The plates were then incubated for 90 min. at room temperature (RT) on a horizontal shaker. 150 µl of HBS with 0.2% BSA and 2% Tween-20 was added to the wells. The plates were then incubated for 60 minutes at RT. 50 µl/well were transferred to a Neutravidin plate and incubated for 30 min at RT on a shaker. The wells were washed with 3×HBS 0.05% Tween-20 and hit on towels after last wash. Anti-EPO-R ab (m.c. R&D) was added diluted 1:400 in HBS+ 0.3% Dry Milk+0.05% Tween-20 repeat pipettor plus. The wells were incubated for 1 hour at RT in a horizontal shaker. The wells were washed 3 times with HBS 0.05% Tween-20 and then hit on towels after last wash. Anti-mouse Ab-HRP (Santa Cruz) was diluted 1:1000, in HBS+0.3% Dry Milk+ 0.05% Tween 20 and added to the wells. Following a 30 min RT incubation, the wells were washed 3 times with HBS 0.05% Tween-20. 100 µl TMB (N,N,N',N'-tetramethyl benzidine) was added and after 15 minutes of RT incubation, 50 µl 2M sulfuric acid was added. The absorbency of the wells was read at 450 nm .

Stock solution aliquots: EPO-R at 2 µM (50 µg/ml PBS) 300 µl/siliconized tube, 60 tubes; ERP-Biotin 50 µl at 1 mM 60 tubes; ERP 120 µl aliquots 60 tubes 1 mM water; make 10×HBS.

Solutions needed for each day: HBS with 2% Tween 20 and 0.2% BSA (500 ml): 10 g Tween-20; 1 g BSA (SIGMA); fill up to 500 ml with HBS; Wash buffer (HBS with 0.05% Tween 20) 1.21 10×HBS; plus 10.81 water; plus 6 g Tween-20 (put Tween first in little beaker dissolve in some water, integrate into volume of water added to the 10×HBS.

Assay buffer: 500 ml Wash buffer plus 0.3% (1.5 g) Safeway Dry Milk;

Cell proliferation:

TF-1 cells were stimulated for 96 hours with different non-peptide EPO-R modulators, and it was observed that the non-peptide EPO binding molecules stimulated cellular proliferation in dose-responsive manner and to the extent of the natural hormone. Results demonstrated that non-peptide EPO-R modulators have anti-apoptotic effect on cells by acting through EPO-R. (See FIG. 3)

Growth and Starvation of UT-7 Cells

UT-7 cells were grown in Minimal Essential Medium Alpha (MEM-α) containing 20% FBS, 1.5 g/L NaHCO$_3$, 5 ng/ml GM-CSF, and 100U Penicillin/100 µg/ml Streptomycin Sulfate ("P/S"), in T150 flasks (60 ml/flask) at 37° C., 5% $CO_2$ to a density of no more than 5×10$^5$ cells/ml. The cells were starved overnight in MEM-α containing 10% FBS, 1.5 g/L NaHCO$_3$ and P/S in T150 flasks (60 ml/flask) at a density of 5×10$^5$ cells/ml, in 5% $CO_2$, 37° C. The cells were then centrifuged in a swinging-bucket rotor at 200×g for 5 minutes at room temperature. The supernatant was removed, and the cells pooled into one 50 ml conical tube. The cells were washed twice with serum-free medium (MEM-α containing 1.5 g/L NaHCO$_3$ and P/S). After the last wash, the cells were resuspended to a density of 1×10$^7$ cells/ml in serum-free medium. The cells were then placed in 15 ml conical tubes in 1 ml aliquots and incubated with the caps loosened for 1 hour at 37° C., 5% $CO_2$. Every 10 minutes, the lower portion of each tube was tapped (flicked) several times to prevent the cells from settling (please note, this step is very important!)

In vitro Signaling:

TF-1 or UT-7 cells were stimulated for up to 30 minutes and activation of EPO-Receptor down stream signaling pathway was evaluated, i.e. phosphorylation of JAK2, STAT1, STAT3 and STAT5. Results demonstrated that non-peptide EPO-R modulators activated EPO-R signal transduction. It was also observed that EPO-R was phosphorylated when stimulated with non-peptide EPO-R modulators. (See FIG. 4)

Signaling in TF-1 Cells in Response to EPO and Compounds

Cell Growth and Starvation: TF-1 cells were grown in RPMI 1640 medium containing 10% FBS, 2 ng/ml human GM-CSF, and 100U Penicillin/100 mg/ml Streptomycin Sulfate ("P/S"), in T150 flasks (60 ml/flask) at 37° C., 5% $CO_2$. The cells were grown to a density of no more than 8×10$^5$ cells/ml. The cells were starved overnight in RPMI 1640 medium containing 3.5% FBS, and P/S in T150 flasks (60 ml/flask) at a density of 8×10$^5$ cells/ml, in 5% $CO_2$, at 37° C. On the day of the assay, before processing the cells, the non-peptide EPO-R modulator to be tested was diluted as described below. The diluted compounds sit at room temperature for 90 min before being added to the cells. The cells were centrifuged in a swinging-bucket rotor at 200×g for 5 min at room temperature. The supernatant was removed and the cells were pooled into one 50 ml conical tube. The cells were washed twice with serum-free medium (RPMI 1640 containing P/S). After the last wash, the cells were resuspended to a density of 1.5×10$^7$ cells/ml in serum-free medium. The cells were placed in 15 ml conical tubes in 1 ml aliquots, and incubated with the caps loosened for 1 hour at 37° C., 5% $CO_2$. Every 10 minutes, the lower portion of each tube was tapped several times to prevent the cells from settling.

Cell Activation and Immunoprecipitation

While the cells were starving, GammaBind G Sepharose beads were coated with antibody. To do this, the Gamma-Bind G beads were washed 3 times with PBS (the beads come in a slurry containing 50% beads; 30 µl of this slurry was used per sample). First, the slurry was spun for 15 to 20 seconds, and the supernatant discarded. For each wash, 1 ml ice cold PBS was added to the beads, and the tube inverted several times. The tube was spun for 15 to 20 seconds, and the supernatant discarded. After the last wash, the supernatant was discarded and 2 µg (10 µl) anti-phosphotyrosine antibody (PY99) per sample was added to the beads. Next, enough PBS was added so that the tube contains 50% beads and 50% liquid (for example, for 10 samples, 300 µl slurry was used; this gives approximately 150 µl beads). The beads were washed and 100 μl antibody plus 50 μl PBS were added. The beads were incubated for 2 hours at room temp with end-over-end rotation.

When the cells finished their 1 hour incubation, they were stimulated as follows: The cells receiving the non-peptide EPO-R modulator have a final DMSO concentration of 0.3%. To maintain equivalent conditions for all cells, DMSO was added to all of the cells that do not receive compounds. To obtain a final concentration of 0.3% DMSO, 10 μl 30% DMSO was added to 1 ml cells and mixed well. 1 ml of cells containing 0.3% DMSO was used as a negative control, and 1 ml of cells containing 300 mU/ml EPO and 0.3% DMSO was used as a positive control.

Dilutions: The samples were diluted to 100× their final concentration and 10 ml of each dilution was added to 1 ml of cells to obtain the final concentration. To obtain a final concentration of 30 μM ERP, 30 μl of the 1 mM stock solution was added directly to 1 ml of cells. For the dilutions, see the table below:

| Final Conc. | 100× | Dilutions |
| --- | --- | --- |
| 300 mU/ml EPO | 30 U/ml | 6 μl 500 U/ml EPO stock + 94 μl ice cold PBS |
| 30 μM Compound | 3 mM | 9 μl 10 mM Compound stock + 21 μl H$_2$O |
| 3 μM Compound | 0.3 mM | 3_1 3 mM Compound + 27 μl 27% DMSO |
| 0.3 μM Compound | 0.03 mM | 4 μl 0.3 mM Compound + 36 μl 27% DMSO |
| 30 μM EPO-R | — | Add 30 μl 1 mM EPO-R stock directly to 1 ml cells |
| 3 μM EPO-R | 0.3 mM | 6 μl 1 mM EPO-R stock + 14 μl ice cold H$_2$O |
| 0.3 μM EPO-R | 0.03 mM | 3 μl 0.3 mM EPO-R (above) + 27 μl ice cold H$_2$O |

The samples were incubated for 30 minutes at 37° C., 5% CO$_2$, and every 10 minutes, the samples were mixed by tapping (flicking) the lower portion of each tube several times. The assays were stopped by adding 14 ml of ice cold PBS to each sample. The samples were centrifuged at 400×g, 4° C. for 5 minutes in a swinging bucket rotor. The samples were placed on ice, and the supernatant was aspirated. To lyse the cells, 800 μl 12× lysis buffer (containing 2× protease inhibitors, added just before use) was added to each cell pellet and pipeted up and down several times. The cells were then incubated on ice for 30 minutes. The samples were transferred into 1.5 ml microcentrifuge tubes, and spun for 10 minutes at 10,000×g, 4° C. While the samples were spinning, the antibody-coated GammaBind G beads were separated into equivalent aliquots in an appropriate number of 1.5 ml microcentrifuge tubes. The supernatant was taken from each sample, and added to the anti-phosphotyrosine-coated GammaBind G beads, and the beads and the supernatant mixture were incubated with end-over-end rotation over night at 4° C. The samples were spun for 15 to 20 seconds, and the supernatant was discarded. The beads were washed twice with 800 μl 1×lysis buffer (containing 1× protease inhibitors, added just before use) and once with 800 μl of a 1:1 mix of lysis buffer: 125 mM Tris pH 6.8 (for each wash, add buffer, invert the tube several times, spin for 15 to 20 seconds, and discard the supernatant). 45 μl 1× sample buffer was added to each sample. The samples were heated for 5 minutes at 95° C., centrifuged briefly (approx. 20 seconds) and examined by SDS-PAGE.

Western Analysis

The samples were run on two 8% SDS-Polyacrylamide gels under reducing conditions. The procedure was to transfer the proteins to Immobilon-P membranes (transfer for 60 min., at 300 mA, in 10 mM CAPS transfer buffer, pH 11 containing 10% MeOH); block the membranes in blotto for 1 hr at room temp; incubate one membrane with α-STAT 5b antibody, and the other with α-EPO-R antibody (dilute both antibodies 1:1,000 in blotto) at 4° C. overnight; wash the membranes 3 times in blotto at room temp., 4 minutes per wash; add α-Rabbit-AP secondary antibody diluted 1:2,000 in blotto to both membranes; incubate for 2 hours at room temp; wash the membranes 3 times with blotto, 4 minutes per wash; wash the membranes twice with 1×TST, 4 minutes per wash; wash the membranes once with 1×TSM, 4 minutes per wash; add 10 ml BCIP/NBT substrate to each membrane for detection.

| Solutions | |
| --- | --- |
| 2 × Lysis Buffer: | |
| 100 mM HEPES, pH 7.6 | 50 ml 1M HEPES, pH 7.6 |
| 300 mM NaCl | 8.8 g NaCl |
| 2% Triton X-100 | 10 ml Triton X-100 |
| 10 mM EDTA | 10 ml 0.5 M EDTA, pH 8 |
| Add H$_2$O to 500 ml | |
| 100 × Protease Inhibitors: | |
| 1 mg/ml Aprotinin | 20 mg Aprotinin |
| 100 μg/ml Pepstatin A* | 2 mg Pepstatin A* |
| 100 μg/ml Leupeptin | 2 mg Leupeptin |
| 100 μg/ml Chymostatin* | 2 mg Chymostatin* |
| 23.8 mg/ml AEBSF | 476 mg AEBSF |
| *Dissolve Chymostatin and Pepstatin-A in 100 μl DMSO before combining with the other inhibitors. Bring volume up to 20 ml in H$_2$O. Add to Lysis Buffer just before using. | |
| Sample Buffer: | |
| 100 μl 50% Glycerol, | |
| 0.05% Bromphenol Blue | |
| 20 μl β-Mercaptoethanol | |
| 40 μl 10% SDS | |
| 160 μl 1 × gel running buffer (electrophoresis buffer) | |
| 10 × TST: | |
| 0.1 M Tris pH 7.4 | 12.1 g Tris base |
| 1.5 M NaCl | 87.7 g NaCl |
| 0.75% Tween-20 | 7.5 ml Tween-20 |
| 0.2% NaN$_3$ | 3 g NaN$_3$ |
| pH to 7.4 | |
| Add H$_2$O to 1 liter | |
| Blotto: | |
| 1 × TST | 100 ml 10 × TST |
| 5 g Dry Milk | 0.5% Dry Milk |
| | Add H$_2$O to 1 liter |
| 10 × TSM: | |
| 1 M Tris pH 9.0 | 121.1 g Tris base |
| 1 M NaCl | 58.4 g NaCl |
| 50 mM MgCl$_2$ | 10.2 g MgCl$_2$× 6H$_2$O |
| pH to 9.0 | |

Dissolve Chymostatin and Pepstatin-A in 100 μl DMSO before combining with the other inhibitors. Bring volume up to 20 ml in H$_2$O. Add to Lysis Buffer just before using.

When the subject compounds were tested for anti-apoptotic effect was evaluated, these antibodies were used: Anti-Bcl-X$_1$/s antibody (Santa Cruz Biotechnology, SC-1041), Anti-Bcl-X$_1$ antibody (Santa Cruz Biotechnology, SC8392)

BCIP/NBT Substrate:

NBT stock: 50 mg/ml in 70% Dimethyl Formamide. Store at −20° C.; BCIP stock: 50 mg/ml in 100% Dimethyl Formamide. Store at −20° C.; Just before using, combine 10 ml 1×TSM with 66 µl 50 mg/ml NBT, and 33 µl 50 mg/ml BCIP; Mix well, and apply to filter.

Materials:

Anti-EPO-R Antibody (c-20): Santa Cruz Biotech, cat. #sc-695; Anti-STAT 5b Antibody (c-17): Santa Cruz Biotech, cat. #sc-835; Anti-Phosphotyrosine Antibody (PY99): Santa Cruz Biotech, cat. #sc-7020; Anti-Rabbit IgG-AP: Santa Cruz Biotech, cat. #sc-2007; BCIP (5-Bromo-4-Chloro-3-Indolyl Phosphate): Sigma, cat. #B-8503; CAPS Buffer (3-[Cyclohexylamino]-1-propanesulfonic acid): Sigma, cat. #C-2632; Fetal Bovine Serum: American Type Culture Collection (ATCC), cat. #30-2020; GammaBind® G Sepharose: Pharmacia Biotech, cat. #17-0885-02; Human GM-CSF: PeproTech, cat. #300-03; Immobilon P: Millipore, cat. #IPVH000010; NBT (Nitro Blue Tetrazolium): Sigma, cat. #N-6876; PBS (Phosphate Buffered Saline): Sigma, cat. #P-3813; Penicillin/Streptomycin Sulfate: Applied Scientific, cat. #9366; RPMI 1640: American Type Culture Collection (ATCC), cat. #30-2001;

Formation of Erythroid Colonies (CFU-e, BFU-e) from Bone Marrow:

Mouse or human bone marrow cells were stimulated in methylcellulose for 7 days (mouse) or 14 days (human) with non-peptide EPO-R modulators. Formation of erythroid colonies was observed. (See FIGS. 6 to 8)

Protocol for Human Bone Marrow Isolation (1) Dilute human bone marrow 1:1 with sterile PBS. (2) Slowly layer bone marrow into 50 ml tubes containing 20 ml of LSM Lymphocyte separation medium (ICN/Cappel—cat #50494). 50 ml bone marrow will yield 2 tubes. (3) Spin tubes at 2000 rpm for 30 minutes with brake off. (4) Slowly take out the middle layer using a 10 ml pipette and transfer into a new 50 ml tube. (5) Add PBS+0.5% BSA+5 mM EDTA to tube for washing. (6) Spin tube for 5 minutes at speed 4 with brake on. (7) Repeat wash step 2 more times. (8) After $3^{rd}$ wash, resuspend pellet in SF Iscoves' MDM medium. (9) Count by diluting cells in 3% acetic acid. (10) Dilute cells to desired concentration ($5\times10^5$ cells/ml) and seed onto methylcellulose.

Protocol for Human Bone Marrow Seeding in Semisolid Methylcellulose Medium (1) Tubes containing 3.0 ml of methylcellulose medium (Stemcell Technology, cat # H4230) supplemented with 50 ng/ml hSCF are prepared. (Alternatively the methylcellulose could be supplemented with 50 ng/ml hSCF, 20 ng/ml of hIL-3 and hIL-6). (2) Compounds or EPO of desired concentrations are added to the tubes. "Control" tubes or tubes that will receive EPO are supplemented with DMSO to a final concentration of 0.16%. The same DMSO concentration is kept constant in all other experimental conditions. (3) 300 µl of human bone marrow cells at $5\times10^5$ cells/ml is added to each tube, vortexed briefly, and the tubes allowed to sit in a test tube rack for 5 minutes. 1.1 ml of the cell mixture is aliquoted into two 35 mm dishes using a 16 g blunt end needle (Stemcell Technology). A third 35 mm dish containing 3 ml of sterile water is placed together with the two dishes into a 125 mm tissue culture dish. (4) The dishes are incubated at 37° C., 5% $CO_2$ and observed periodically for colony formation. Colonies are scored on day twelve.

Colony Formation Assay

Bone marrow cells were isolated from mouse femurs. Cells were washed twice with PBS and resuspended to a density of $6.5\times10^6$ cells/ml in media. 300 µl ($6.5\times10^5$/ml) of cells were mixed with 1.5 ml of methylcellulose media (Stemcell Technology) to which the desired concentration of compound or the EPO was added. The mixture was poured onto 35 mm dishes; all the conditions are performed in duplicates. The incubation was for eight days at 37° C., 5% $CO_2$. The colonies were scored on day seven.

Materials:

Stemcell Technology: 1. Methycellulose base medium for murine cells cat# M3234 80 ml/bottle; 2. 35 mm dish cat# 27150 500/pack cat# 27100 10/pack; 3. Iscove's Modified Dulbecco's Medium (MDM) with 2% FBS cat# 07700 100 ml/bottle; 4. 16 gauge blunt-end needle cat# 28110 pack of 100; 5. 3 cc syringes cat# 28240 pack of 1000; 6. Gridded scoring dishes cat# 27500 5/pack;

Applied Scientific: 1. minisorp tube 100×15 cat# 468608; 2. minisorp tube 100×15 stopper cat# 343036; 3. 10 cc syringe cat# 9604;

Corning: 1. sterile 100 mm tissue culture dish cat# 25020;

Additional materials: 1. sterile water; 2. counter.

After thawing methylcellulose overnight, the next morning, 20 ml of Iscove's MDM+2%FBS is added to the bottle to achieve 100 ml total. The bottle is mixed for at least 30 seconds and settled for about 10 minutes. 10 cc syringes are used to aliquot 3 ml per minisorp tube.

CFU-e Formation from Fetal Liver Cells

Mouse fetal liver cells were isolated and stimulated in methylcellulose with non-peptide EPO-R modulators for 3 days. Formation of erythroid colonies was observed (See FIG. 5)

Mouse Fetal Liver CFU-e Assays

The procedure was as follows. 1. Remove fetuses from 1 to 2 E12 Timed pregnant CD-1 mice (10–12 fetuses; Charles River) into ice cold IMDM (StemCell Tech) in a 10-cm dish; 2. Dissect out fetal liver (FL) from fetuses in IMDM under a dissection scope; 3. Wash FL 2× with IMDM; 4. Add 1–2 mL IMDM; disaggregate the FL into cell suspension by pipeting up/down with a P1000/blue tip 10–15 times; 5. Pass the cell suspension through a Cell Strainer (70u, Falcon 352350); 6. Wash cells 3× in IMDM; Resuspend cells in 1 mL IMDM/2% FBS (StemCell) and count nucleated cells $\frac{1}{20}$ in 3% acetic acid; 12 FL should yield around $4\times10^7$ nucleated cells; 7. Dilute FL cells in IMDM/2% FBS to $0.5–1\times10^6$/mL; 8. Add 0.3 ml cells into 3 mL 1×M3231 (StemCell Technologies) containing recombinant human erythropoietin alpha and/or other cytokines/compounds; 9. Vortex vigorously and let stand for 5 minutes; 10. Dispense 2×1.1 mL into 35-mm dishes (StemCell #27100) using a 16-gauge blunt-end needle/3 mL syringe; 11. Place the 2 35-mm dishes into a 10-cm culture dish along with a third uncovered 35-mm dish containing 3 mL sterile water; 12. Incubate 2–3 days at 37C/5% $CO_2$ and score for CFU-e.

Optional: Benzidine Staining of CFU-e/BFU-e

1. Make benzidine staining soln (make up fresh)—0.2% Benzidine HCl (Sigma B-3383), 0.5% glacial acetic acid, 0.12% $H_2O_2$ (0.2 mL/50 mL 30% H2O2, Sigma H-1009); 2. Gently add sufficient amount (0.75 mL/35 mm dish) of benzidine staining solution into Methocult dishes to cover the cells; Wait a few minutes; cells expressing hemoglobin will turn blue.

In vivo Experiments with Anemic Animals

Figure 10:
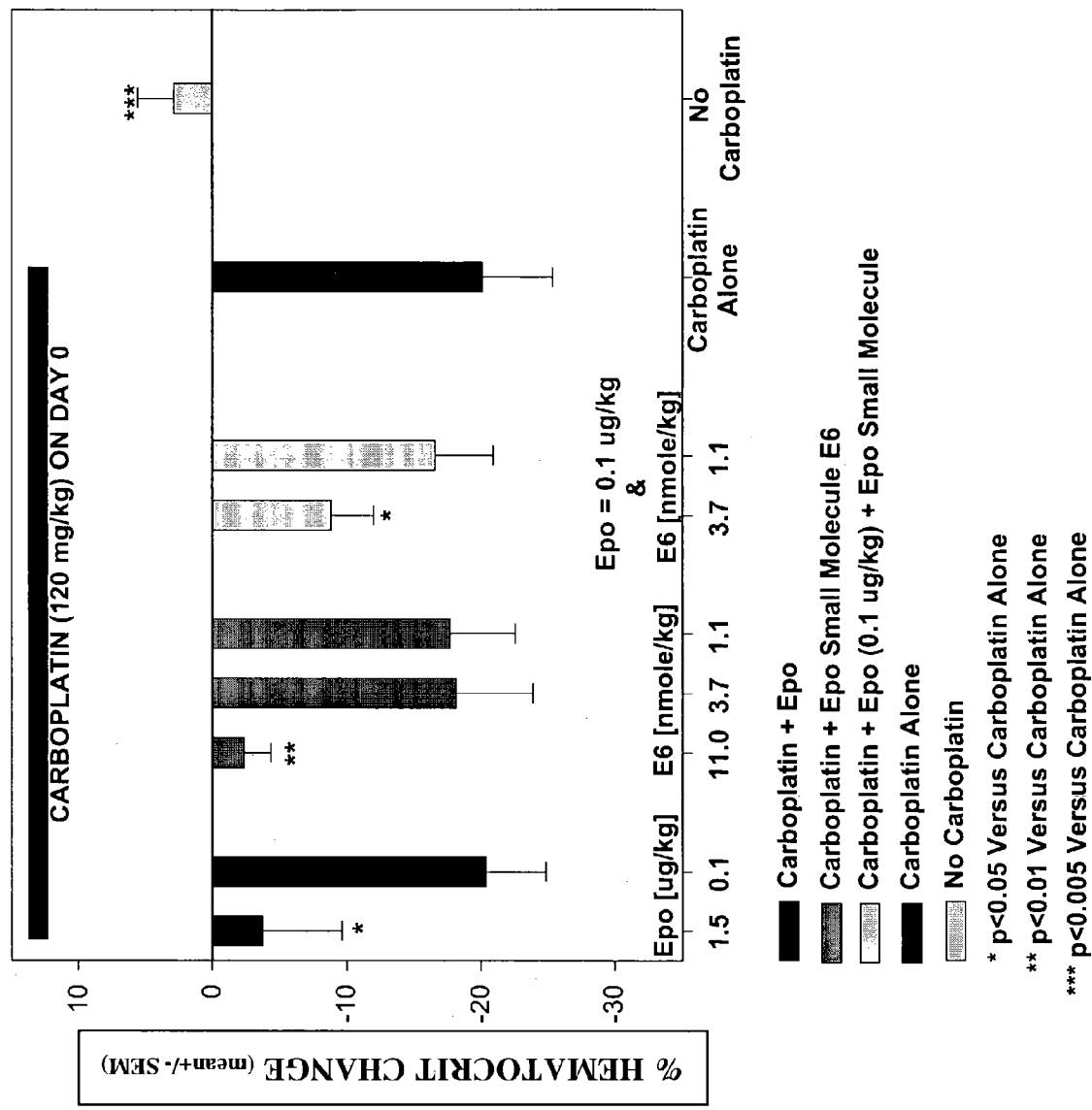
FIG. 10 shows the cooperative effect between non-peptide EPO-R modulator E6 and EPO on hematocrit levels in carboplatin-treated 8 week old C57BL mice. The compound was given i.p.
Figure 11:
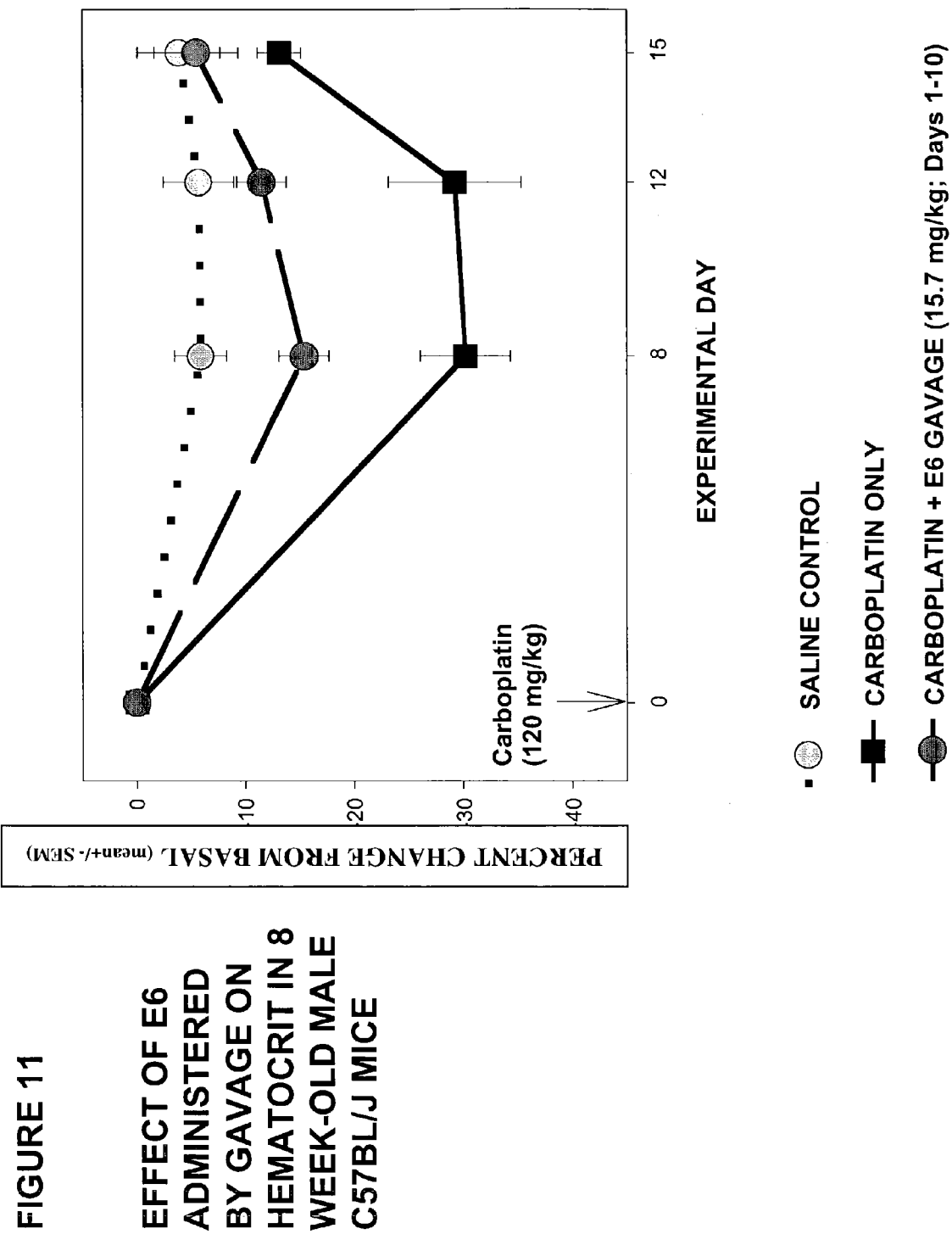
FIG. 11 shows the effect of non-peptide EPO-R modulator E6 on hematocrit levels in carboplatin-treated 8 week old C57BL mice. The compound was given orally.

Mice were treated with Carboplatin agent (available from Sigma, used regularly in chemotherapy) and a drop in hematocrit was induced. Intraperitoneal (ip) or oral administration of non-peptide EPO-R modulators protected from a drop in hematocrit levels of Carboplatin treated animals; i.e. at least partially prevented development of anemia. (FIGS. 9–11)

Determination of Effect of Non-peptide EPO-R Binding Small Molecule on Hematocrit in Carboplatin-Induced Anemia in 8 Week C57Bl Male Mice Injection Protocol Preparation of injection solutions: Vehicle—Saline with 0.1 mg/mL BSA; Add 30 mg of BSA to 300 mL Saline ; Vacuum filter under sterile conditions in laminar flow hood; Aliquot the saline (0.1 mg/mL BSA) solution into mini-sorp tubes. At least 41×7 mL aliquots should be prepared. Place caps on the tubes and store refrigerated at 4° C.;

Carboplatin—Dose of 120 mg/kg: Calculations for single injection given to 36 male mice (8 wks old~25 g): 120 mg/mouse×0.025 kg×36 mice=108 mg; Injections are delivered i.p. in a volume of 0.5 cc/mouse=0.5 cc/mouse×36 mice=18 cc; Carboplatin at 6 mg/mL for 36 mice: 108 mg/18 cc.; 120 mg/20 cc; On day of injection, add 120 mg carboplatin (Sigma #C2538) to 20 cc saline in a 100 cc beaker containing a stirring bar. Cover beaker with parafilm. Mix until the carboplatin has completely dissolved.

Non-peptide EPO-R Binding Small Molecule—Dose at 11 nmole/kg/day

Calculations for daily injections given to 12 male mice (8 wks old~25 g) over a period of 10 days:

11 nmole/kg/mouse/day×0.025 kg×12 mice=3.3 nmoles/day; Injections are delivered i.p. in a volume of 0.5 cc/mouse/day=0.5cc/mouse/day×12 mice=6 cc/day; non-peptide EPO-R binding small molecule for 20 mice: 3.3 nmoles/6 cc each day: 3.85 nmole/7 cc each day; non-peptide EPO-R binding small molecule aliquot at 2 mM=2 nmole/μL; 3.85 nmole per day in 7 cc (0.55 nmole/mL); Therefore: 3.85 nmole divided by 2 nmole/μL stock=1.925 μL at 2 mM; Prepare in advance at least 10 aliquots of non-peptide EPO-R binding small molecule at 2 mM in small microfuge tubes, each with a volume of 2 μL. Freeze these aliquots; On each day of injections, add 1 thawed aliquot of the non-peptide EPO-R binding small molecule at 2 mM containing a 2 μL volume to a tube containing 7 cc of sterile saline (0.1 mg/mL BSA). This results in an non-peptide EPO-R binding small molecule injection solution with 0.55 nmole/mL concentration.

Erythropoietin Dose at 1.5 μg/kg/day: Calculations for daily injections given to 12 male mice (8 wks old~25 g) over a period of 10 days: 1.5 μg/kg/mouse/day×0.025 kg×12 mice=0.45 μg/day; Injections are delivered i.p. in a volume of 0.5 cc/mouse/day=0.5cc/mouse/day×12 mice=6 cc/day; EPO for 12 mice: 0.45 μg/6 cc each day: 0.525 μg/7 cc each day; Reconstitute 500 units (5 μg) of EPO (#287-TC-500, R&D Systems) with 1 mL PBS to provide a stock concentration at 5 μg/mL; Use 0.525 μg per day in 7 cc (75 ng/mL); Therefore: 0.525 μg divided by 5 μg/mL stock=0.105 mL at 5 μg/mL~100 μL at 5 μg/mL; Prepare in advance at least 10 aliquots of EPO at 5 μg/mL in small microfuge tubes, each with a volume of 100 μL. Freeze these aliquots; On each day of injections, add 1 thawed aliquot of the EPO at 5 μg/mL with a volume of 100 μL to a tube containing 7 cc of sterile saline (0.1 mg/mL BSA). This results in an erythropoietin injection solution with a concentration of 75 ng/mL.

Injection Regimen

Carboplatin Only Negative Control Group: Each animal is given a 0.5 cc i.p. injection of carboplatin at 6 mg/mL on day 0. Each animal is given a 0.5 cc i.p. injection of saline (0.1 mg/mL BSA) on days 1 through 10.

Injection Regimen

Carboplatin+non-peptide EPO-R binding small molecule (11 nmole/kg/day) Test Group: Each animal is given a 0.5 cc i.p. injection of carboplatin at 6 mg/mL on day 0. Each animal is given a 0.5 cc i.p. injection of non-peptide EPO-R binding small molecule (0.55 nmole/mL) on days 1 through 10.

Carboplatin+Erythropoictin (1.5 μg/kg/day) Positive Control Group: Each animal is given a 0.5 cc i.p. injection of carboplatin at 6 mg/mL on day 0. Each animal is given a 0.5 cc i.p. injection of Erythorpoietin at 75 ng/mL on days 1 through 10.

Saline Control Group: Each animal is given a 0.5 cc i.p. injection of saline (0.1 mg/mL BSA) on day 0. Each animal is given a 0.5 cc i.p. injection of saline (0.1 mg/mL BSA) on days 1 through 10.

Reticulocyte Measurement in Normal Mice

Figure 12:
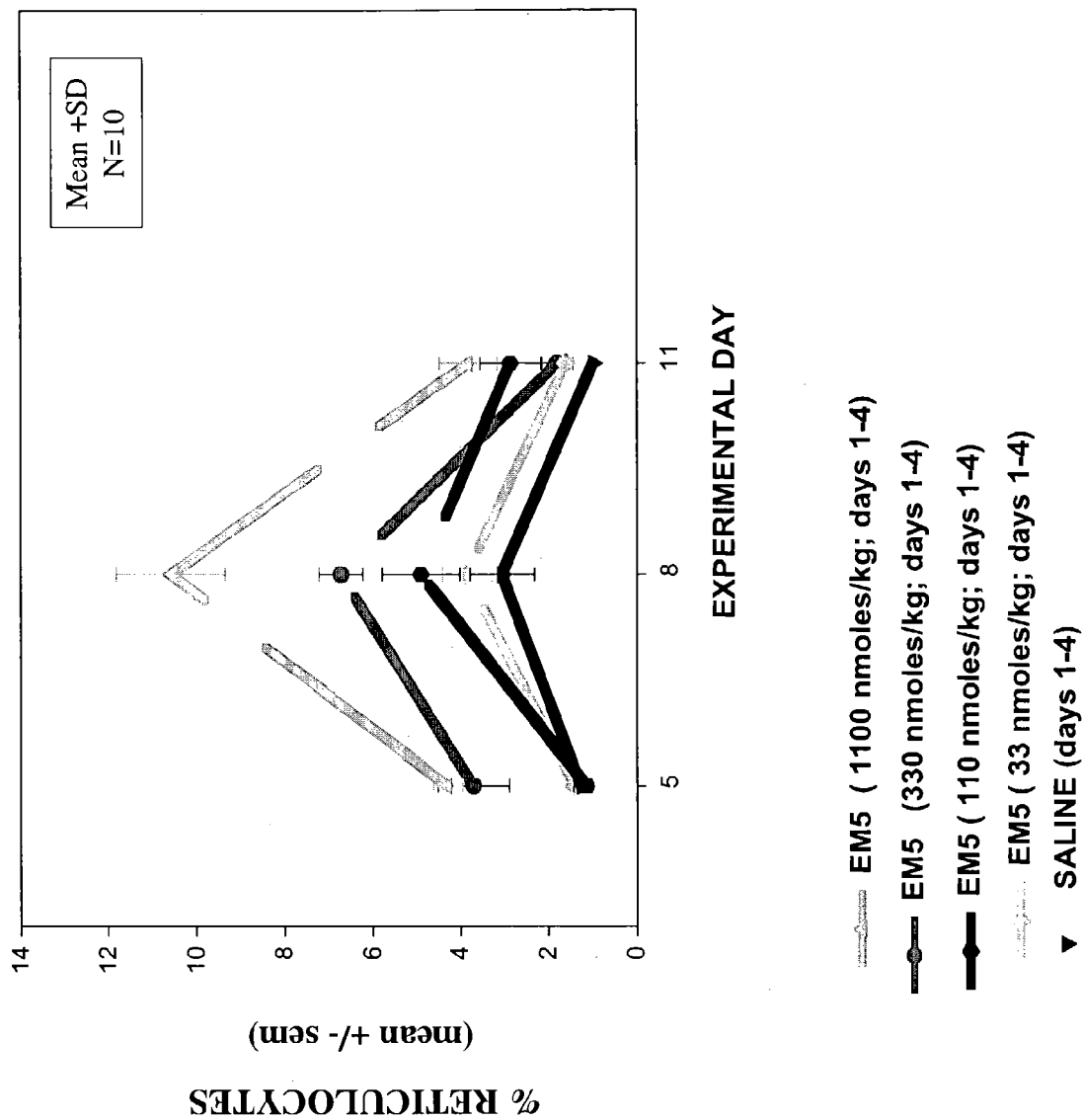
FIG. 12 shows the effect of non-peptide EPO-R modulator E5 on reticulocyte levels in normal mice. The compound was given i.p.

Normal mice were injected ip with non-peptide EPO-R modulators on day 0. Reticulocyte levels were measured on days 5, 8, and 11 after injections. Non-peptide EPO-R modulators increased reticulocyte levels to the same extent as the natural hormone.(See FIG. 12)

Small molecules that act as a replacement and in cooperation with EPO were evaluated for their potential application in CNS. The results obtained indicated that indeed, the subject small molecules have a protective role in neuronal apoptosis. The subject small molecules tested protected the cultured neurons from glutamate neurotoxicity by increasing the cell survival by 60%. Thus, the subject small molecules can find use in prevention of cerebral ischemia, spinal cord injury or metabolic stress.

A number of molecules of the subject invention were evaluated in in vitro systems that reflect the condition of cerebral ischemia and metabolic stress. Firstly, it is known that one of the mechanisms by which EPO prevents neuronal apoptosis is by up-regulating the expression levels of Bcl-$x_1$ protein, which is a well-described anti-apoptotic protein. Thus, cells-lines that are known to be EPO responsive (UT-7 and TF-1, used in previous studies) were used as a cellular system to examine the small molecules' anti-apoptotic activity through EPO-R.

Application of Subject Small Molecules in CNS System

As presented in FIGS. 13–14, in both cell lines, small molecules (E5A24 and EM5) induced up-regulation of Bcl-$x_1$ protein in a dose-responsive manner. Achieved up-regulation of Bcl-$x_1$ protein was to the levels achieved with EPO. The evaluation was performed by starving the cells, stimulating the cells with compounds at appropriate concentrations (or no stimulation for control samples) and immuno-precipitating the cell lysates with antibody specific to both forms (short and long) of Bcl-$x_1$ protein. The amount of Bcl-$x_l$ (long protein form, known to have anti-apoptotic activity) protein was evaluated by western blot analysis.

Experiments were performed according to the described protocol. The anti-apoptotic effect of the subject small molecules was evaluated in P-19 cells (a neural-like embryonal carcinoma cell line) that undergo apoptosis upon withdrawal of serum. Briefly, cells were treated with small molecules for 24 hours prior to serum withdrawal. Serum was withdrawn for 48 hours in the presence or absence of a subject small molecule (EM5 and E5A24). At the end of that period, cell survival was evaluated. As presented on FIG. 15, small molecules, in a dose-responsive manner, protect cells from apoptosis. This Figure is representative of the experiment and of the subject small molecules. The experiments were performed according to literature procedures (Siren et.al., Proc. Nat. Acad. Sci. 98, 4044, 2001). Cell survival was determined according to the protocol described for cellular proliferation.

Primary cultured cells were used as a model to evaluate the subject small molecule effect on CNS. Glutamate neurotoxicity can be most directly studied using neurons prepared from the brain at the late embryonic stage and subsequently cultured for maturation. To examine the effect of the subject small molecules (E5A24 and E5A29) on glutamate-induced neuronal death, cortical neurons isolated from embryonic day 18 rats, were cultured for 10 days.

Subsequently, neurons were treated for 24 hours with or without the subject small molecules, and further exposed to 300 μM glutamate for 24 hours. After glutamate was washed out, the cells were cultured for another 24 hours. During the glutamate challenge and subsequent culture, the subject small molecules were absent. Finally, the cell viability was examined. FIG. 16 shows that subject small molecules will increase cell survival by 60%. Thus, small molecules prevented glutamate induced neuronal death in a dose-responsive manner. Experiments were performed according to the literature (Morishita et. al., Neuroscience 76, 105, 1997).

The above results demonstrate the extraordinary capability of the subject family of compounds to bind specifically to the modulation domain of EPO-R with high affinity. By using non-peptide compounds that have significant stability under a variety of conditions, including physiological and cellular conditions, one can purify EPO-R, assay for changes in the amount of EPO-R present, particularly at a cell surface, in response to changes in environment, e.g. test compounds, without interfering with binding of a ligand. One can also determine whether a test ligand and a subject compound act together to enhance the activity of EPO-R signal transduction, with concentrations of the EPO-R ligand below saturation.

In addition, subject compounds have been found to be effective with a variety of cells that express EPO-R inducing a signal into the cell upon binding to the modulating domain of the EPO-R. The subject compounds may be used individually or in combination with each other or EPO in inducing a signal.

The subject compounds, individually or in combination with EPO can be used for enhancing hematocrit, allowing for reduced levels of EPO to achieve the same enhancement of hematocrit. The compounds were found safe with an exemplary labortory animal, there being no observed toxic events, while at the same time being able to correct induced anemia.

The subject compounds can be used with neuronal cells to modulate apoptosis. Their small size and lipophilicity enhance their ability to cross the blood-brain barrier. When endogenous EPO is deficient, the subject compounds will serve to protect the neuronal cells. In a recognized test, the subject compounds were found to enhance survival of cells in a neurotoxic environment. As EPO-R is found on other cells in different contexts, the subject compounds can find use in modulating the response of the cells in relation to a context that is affected by the presence or absence of EPO.

Because the subject compounds are not readily degraded in the intestinal tract or in the blood, the subject compounds can be administered orally, as well as parenterally. In addition, the subject compounds can be used for investigating other compounds, such as biosteres, that have analogous effects with EPO-R, but may enjoy improvements in bioavailability, potential side effects, idiosyncratic responses and higher affinity, resulting in lower dosages.

The subject compounds can be readily prepared in high yield following known synthetic procedures. They share similarities with known drugs having physiological activity, so they can be readily formulated in accordance with known methodologies. They find application whenever and wherever one wishes to modulate EPO-R activity.

All references referred to in the text are incorporated herein by reference as if fully set forth herein. The relevant portions associated with this document will be evident to those of skill in the art. Any discrepancies between this application and such reference will be resolved in favor of the view set forth in this application.

Although the invention has been described with reference to the above examples, it will be understood that modifications and variations are encompassed within the spirit and scope of the invention. Accordingly, the invention is limited only by the following claims.

---

What is claimed is:

1. A pharmaceutical composition comprising in an effective amount for modulating EPO-R activity:
a non-peptide organic molecule of from 12 to 36 atoms other than hydrogen, from 9 to 20 carbon atoms, from 4 to 12 of the heteroatoms chalcogen, nitrogen, halogen, and metal ion of Groups I or II of the periodic chart,
wherein said non-peptide organic molecule is of the formula (1):

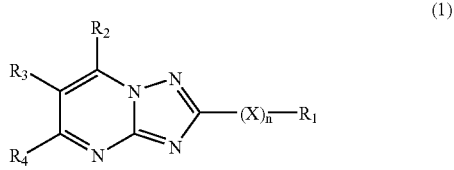

(1)

wherein:
X is of from 1 to 3 atoms other than hydrogen, and is amino, alkyl substituted amino, oxygen, or sulfur bonded to 0 to 2 oxygen atoms;
n is 0 or 1;
$R_1$ is substituted phenyl having from 0 to 3 substituents that are $CH_3$, Cl, $NO_2$, or $CF_3$, and $R_1$ is optionally bonded directly to an annular carbon atom or through a linking group of from 1 to 3 carbon and nitrogen atoms or N-hydroxyamidinyl;
$R_2$ is $CH_3$, $NH_2$, OH, or aroylamido of from 7 to 8 carbon atoms having optional substituents that are $CH_3$, Cl, $NO_2$, or $CF_3$;
$R_3$ is H, carboxy, or unsubstituted or halo substituted cycloalkylalkyl of from 4 to 8 carbon atoms, having from 3 to 4 annular atoms;
$R_4$ is H, unsubstituted or halo substituted lower alkyl of from 1 to 3 carbon atoms, or alkoxymethyl of from 2 to 4 carbon atoms;
with the proviso that $R_3$ and $R_4$ may be taken together to define 1,2-dimethylene-alpha-halo, or alpha-$CH_3$-halobenzene, where halo is F or Cl; and
a pharmaceutically acceptable vehicle.

2. A pharmaceutical composition comprising in an effective amount for modulating EPO-R activity:
a non-peptide organic molecule of from 12 to 36 atoms other than hydrogen, from 9 to 20 carbon atoms, from 4 to 12 of the heteroatoms chalcogen, nitrogen, halogen, and metal ion of Groups I or II of the periodic chart,
wherein said non-peptide organic molecule is of the formula (3):

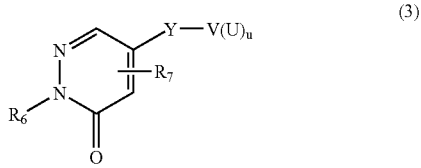

(3)

wherein:
Y is amino, $CH_2$, O, or $S(O)_m$, where m is 0, 1 or 2;
$R_6$ is H or alkyl of from 1 to 3 carbon atoms;
$R_7$ is H, or a group of from 0 to 3 atoms other than hydrogen, and is oxy, thio, amino, nitro, cyano or alkyl;
V is a phenyl group;
U is a group of from 0 to 3 atoms other than hydrogen, and is oxy, thio, amino, nitro, cyano, halo or alkyl;
u is 0 to 3; and
a pharmaceutically acceptable vehicle.

3. A pharmaceutical composition comprising in an effective amount for modulating EPO-R activity:
a non-peptide diazolohydroquinoline organic molecule of from 12 to 36 atoms other than hydrogen, from 9 to 20 carbon atoms, from 4 to 12 of the heteroatoms chalcogen, nitrogen, halogen, and metal ion of Groups I or II of the periodic chart,
wherein said non-peptide diazolohydroquinoline organic molecule is of the formula (4):

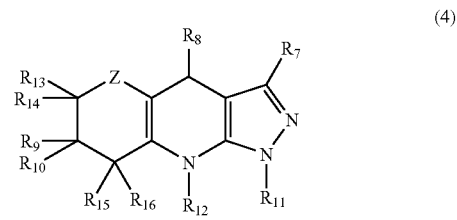

(4)

wherein:
Z is $CH_2$, C=O, C=S, C=NH, or CH-alkyl, wherein alkyl is of from 1 to 3 carbon atoms;
$R_7$ is H or an organic group of from 1 to 12 carbon atoms and 0 to 4 heteroatoms;
$R_8$ is H, an aliphatic group of from 1 to 6 carbon atoms, or a heterocycle of from 5 to 6 annular members and from 1 to 2 heteroannular members that are O, N, or S;
$R_9$, $R_{10}$, $R_{13}$, $R_{14}$, $R_{15}$ and $R_{16}$ are the same or different and are H, an organic radical of from 1 to 12 carbon atoms or a heterosubstituent of from 1 to 3 heteroatoms;
$R_{11}$ and $R_{12}$ are the same or different and are H or an organic group of from 1 to 12 carbon atoms; and
a pharmaceutically acceptable vehicle.

4. The pharmaceutical composition according to claim 3, wherein said diazolohydroquinoline is of the formula:

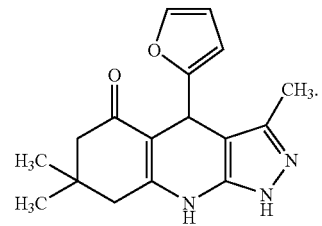

5. An EPO receptor complex having a polypeptide comprising:
the modulating domain sequence of erythropoietin receptor; and
a non-peptide organic molecule of from 12 to 36 atoms other than hydrogen, from 9 to 20 carbon atoms, from 4 to 12 of the heteroatoms chalcogen, nitrogen, halogen, and metal ion of Groups I or II of the periodic chart,
wherein said non-peptide organic molecule is of the formula (1):

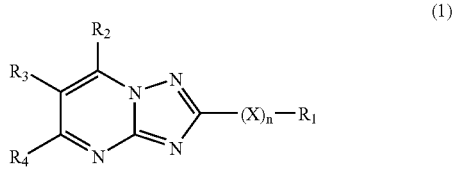

(1)

wherein:
X is of from 1 to 3 atoms other than hydrogen, and is amino, alkyl substituted amino, oxygen, or sulfur bonded to 0 to 2 oxygen atoms;
n is 0 or 1;
$R_1$ is alkyl of from 1 to 3 carbon atoms, or an organic group having a six annular membered aromatic group having from 0 to 3 substituents, where the substituents are halo, lower alkyl of from 1 to 3 carbon atoms, $NO_2$, or trihalomethyl, and $R_1$ is bonded directly to X or bonded through a linking group of from 1 to 4 carbon, nitrogen, or chalcogen atoms in a chain, there being from 0 to 2 heteroatoms in the chain, where the heteroatoms are bonded solely to carbon and hydrogen, or alpha-acetamidinyl having from 0 to 1 N—OH;
$R_2$ is H, alkylamino of from 0 to 3 carbon atoms, alkoxy of from 0 to 3 carbon atoms, or a heterofunctionality having nitrogen or chalcogen bonded to annular carbon which is substituted with an organic group of from 1 to 10 carbon atoms and from 0 to 3 heteroatoms;
$R_3$ is H or an organic group of from 1 to 10 carbon atoms and from 0 to 4 chalcogen, halo or nitrogen heteroatoms;
$R_4$ is H, or optionally substituted alkyl of from 1 to 6 carbon atoms, where the substituents are oxy, amino or halo;
with the proviso that $R_3$ and $R_4$ may be taken together to form a ring with the annular atoms to which they are attached of from 4 to 10 annular atoms and forming from 1 to 2 rings, where the annular atoms are unsubstituted or substituted with halo, alkyl of from 1 to 3 carbon atoms, alkoxy of from 0 to 3 carbon atoms, thioalkyl of from 0 to 3 carbon atoms, or alkyl amino of from 0 to 4 carbon atoms.

6. The complex according to claim 5, wherein $R_3$ is H or an organic group of from 1 to 8 carbon atoms and 0 to 4 chalcogen, halo, or nitrogen heteroatoms.

7. The complex according to claim 6, wherein $R_3$ is cyclopropylmethylamino.

8. The complex according to claim 6, wherein $R_3$ is H.

9. The complex according to claim 6, wherein $R_1$ is a six annular membered aromatic group having 0 to 3 substituents, where the substituents are halo, lower alkyl of from 1 to 3 carbon atoms, nitro or trihalomethyl, and is either directly bonded to X or bonded through a linking group of from 1 to 4 carbon, nitrogen, or chalcogen atoms in a chain.

10. The complex according to claim 6, wherein $R_4$ is methyl.

11. The complex according to claim 6, wherein $R_4$ is H.

12. An EPO receptor complex having a polypeptide comprising:
the modulating domain sequence of erythropoietin receptor; and
a non-peptide organic molecule of from 12 to 36 atoms other than hydrogen, from 9 to 20 carbon atoms, from 4 to 12 of the heteroatoms chalcogen, nitrogen, halogen, and metal ion of Groups I or II of the periodic chart,
wherein said non-peptide organic molecule is of the formula (1):

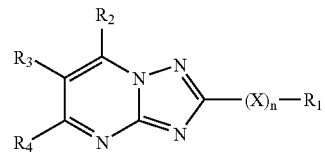

(1)

wherein:
X is from 1 to 7 atoms other than hydrogen, and is amino, alkyl substituted amino, oxygen, or sulfur bond bonded to 0 to 2 oxygen atoms;
n is 0 or 1;
$R_1$ is alkyl of from 1 to 3 carbon atoms, or substituted phenyl having from 0 to 3 substituents that are $CH_3$, Cl, $NO_2$, or $CF_3$, and $R_1$ is bonded directly to an annular carbon atom or through a linking group of from 1 to 3 carbon and nitrogen atoms or N-hydroxyamidinyl;
$R_2$ is $CH_3$, $NH_2$, OH, or aroylamido of from 7 to 8 carbon atoms having substituents that are $CH_3$, Cl, $NO_2$, or $CF_3$;
$R_3$ is H, carboxy, or unsubstituted or halo substituted cycloalkylalkyl of from 4 to 8 carbon atoms, having from 3 to 4 annular atoms;
$R_4$ is H, unsubstituted or halo substituted lower alkyl of from 1 to 3 carbon atoms, or alkoxymethyl of from 2 to 4 carbon atoms;
With the proviso that $R_3$ and $R_4$ may be taken together to define 1,2-dimethylene-alpha-halo, or alpha-$CH_3$-halobenzene, where halo is F or Cl.

13. An EPO receptor complex having a polypeptide comprising:
the modulating domain sequence of erythropoietin receptor; and
a non-peptide organic molecule of from 12 to 36 atoms other than hydrogen, from 9 to 20 carbon atoms, from 4 to 12 of the heteroatoms chalcogen, nitrogen, halogen, and metal ion of Groups I or II of the periodic chart,
wherein said non-peptide organic molecule is of the formula:

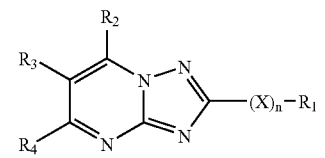

(1)

wherein:

X is from 1 to 7 atoms other than hydrogen, and is amino, alkyl substituted amino, oxygen, or sulfur bond bonded to 0 to 2 oxygen atoms;

n is 0 or 1;

$R_1$ is organic group of from 1 to 12 carbon atoms and from 0 to 6 heteroatoms, which are chalcogen, nitrogen, or halogen, said organic group further comprising an aliphatic group of from 1 to 6 carbon atoms having from 0 to 2 sites of unsaturation, non-oxo-carbonyl and the nitrogen and sulfur derivatives thereof, alicyclic group having from 0 to 2 sites of unsaturation, aryl group, heterocyclic group and combinations thereof where the cyclic structures may have from 1 to 2 rings;

$R_2$ is H, a heterofunctionality having nitrogen and/or chalcogen bonded to annular carbon to which is substituted with an organic group of from 1 to 10 carbon atoms, aryl, alkaryl, aralkyl, and aralkenyl of from 5 to 10 carbon atoms, aroyl of from 6 to 10 carbon atoms, or an organic group bonded through a carbon atom of from 1 to 12 carbon atoms having from 1 to 4 heteroatoms, which are chalcogen, nitrogen, or halogen;

$R_3$ is H or an organic group of from 1 to 10 carbon atoms and from 0 to 4 chalcogen and nitrogen heteroatoms;

$R_4$ is H, alkyl, or substituted alkyl of from 1 to 6 carbon atoms, where the substituents are oxy, amino or halo;

With the proviso that $R_3$ and $R_4$ may be taken together to form a ring with the annular atoms to which they are attached of from 4 to 10 annular atoms and forming from 1 to 2 rings, where the annular atoms are unsubstituted or substituted with halo, alkyl of from 1 to 3 carbon atoms, alkoxy of from 0 to 3 carbon atoms, thioalkyl of from 0 to 3 carbon atoms and alkylamino of from 0 to 4 carbon atoms;

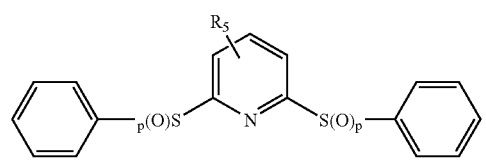

(2)

wherein:

p is 0, 1, or 2;

$R_5$ has from 1 to 3 atoms other than hydrogen, and is oxy, thio, amino, nitro, cyano, or alkyl;

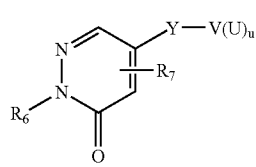

(3)

wherin:

Y is amino, $CH_2$, O, or $S(O)_m$, wherein m is 0, 1, or 2;

V is an aryl group having 6 annular members comprising 0 to 2 nitrogen atoms, the remainder being carbon atoms;

U is a substituent of from 0 to 5 atoms other than H, and is oxy, thio, amino, nitro, cyano, halo, or alkyl;

u is 0 to 3;

$R_6$ is H or alkyl of from 1 to 3 carbon atoms;

$R_7$ is H or a group having 0 to 3 atoms other than H, and is oxy, thio, amino, nitro, cyano, or alkyl; or

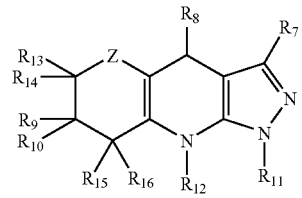

(4)

wherein:

Z is $CH_2$, C=O, C=S, C=NH, or CH-alkyl, wherein alkyl is of from 1 to 3 carbon atoms;

$R_7$ is H or an organic group of from 1 to 12 carbon atoms and 0 to 4 heteroatoms;

$R_8$ is H, an aliphatic group of from 1 to 6 carbon atoms, or a heterocycle of from 5 to 6 annular members and from 1 to 2 heteroannular members that are O, N, or S;

$R_9$, $R_{10}$, $R_{13}$, $R_{14}$, $R_{15}$ and $R_{16}$ are the same or different and are H, an organic radical of from 1 to 12 carbon atoms or a heterosubstituent of from 1 to 3 heteroatoms;

$R_{11}$ and $R_{12}$ are the same or different and are H or an organic group of from 1 to 12 carbon atoms.

14. A complex according to claim 13, wherein said polypeptide and said non-peptide organic molecule are complexed at the modulating domain of EPO-R.

15. A complex according to claim 14, wherein said polypeptide is EPO-R bound to a cellular membrane.

16. A complex according to claim 13, wherein the non-peptide organic molecule is a diazolohexahydroquinoline of formula (4).

17. A complex according to claim 16, wherein the diazolohexahydroquinoline is of the formula:

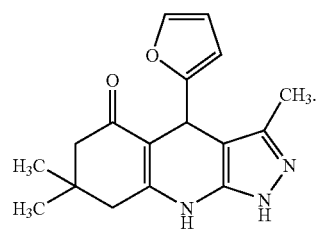

18. An EPO receptor complex having a polypeptide comprising:

the modulating domain sequence of erythropoietin receptor; and a non-peptide organic molecule of from 12 to 36 atoms other than hydrogen, from 9 to 20 carbon atoms, from 4 to 12 of the heteroatoms chalcogen, nitrogen, halogen, and metal ion of Groups I or II of the periodic chart, wherein said non-peptide organic molecule is of the formula:

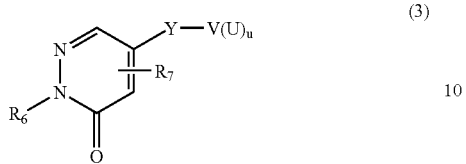

(3)

wherein:
Y is amino, $CH_2$, O, or $S(O)_m$, where m is 0, 1 or 2;
$R_6$ is H or alkyl of from 1 to 3 carbon atoms;
$R_7$ is H, or a group of from 0 to 3 atoms other than hydrogen, and is oxy, thio, amino, nitro, cyano or alkyl;
V is a phenyl group;
U is a group of from 0 to 3 atoms other than hydrogen, and is oxy, thio, amino, nitro, cyano, halo or alkyl; and
u is 0 to 3.

19. The complex according to claim 18, wherein Y is $SO_2$, $R_7$ is Cl, and u is 0.

20. A method for determining the binding affinity of a test compound to the modulating domain of EPO-R, said method comprising:
adding said test compound to a complex according to claim 13; and
determining the amount of complex of said complex in the presence of said test compound as compared to the absence of said test compound.

21. A method of inducing a physiological response of EPO-R in a host, the method comprising: administering to said host a physiologically effective amount of a non-peptide organic molecule of from 12 to 36 atoms other than hydrogen, from 9 to 20 carbon atoms, from 4 to 12 of the heteroatoms chalcogen, nitrogen, halogen, and metal ion of Groups I or II of the periodic chart, wherein said non-peptide organic molecule is of the formula:

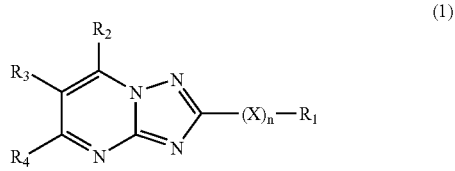

(1)

wherein:
X is of from 1 to 3 atoms other than hydrogen, and is amino, alkyl substituted amino, oxygen, or sulfur bonded to 0 to 2 oxygen atoms;
n is 0 or 1;
$R_1$ is alkyl of from 1 to 3 carbon atoms, substituted phenyl having from 0 to 3 substituents that are $CH_3$, Cl, $NO_2$, or $CF_3$, and $R_1$ is bonded directly to an annular carbon atom or through a linking group of from 1 to 3 carbon and nitrogen atoms in a chain, or N-hydroxamindinyl;
$R_2$ is $CH_3$, $NH_2$, OH, or aroylamido of from 7 to 8 carbon atoms having from 0 to 2 substituents that are $CH_3$, Cl, $NO_2$, or $CF_3$;

$R_3$ is H, carboxy, or cycloalkylalkyl of from 4 to 8 carbon atoms, having from 3 to 4 annular atoms;
$R_4$ is H, unsubstituted or halo substituted lower alkyl of from 1 to 3 carbon atoms, or alkoxymethyl of from 2 to 4 carbon atoms;
with the proviso that $R_3$ and $R_1$ may be taken together to define 1,2-dimethylene-alpha-halo, or alpha-$CH_3$-halobenzene, where halo is F or Cl; or

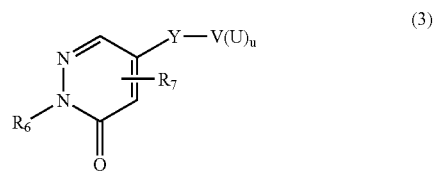

(3)

wherein:
Y is amino, $CH_2$, O, or $S(O)_m$, where m is 0, 1 or 2;
$R_6$ is H or alkyl of from 1 to 3 carbon atoms;
$R_7$ is H, or a group of from 0 to 3 atoms other than hydrogen, and is oxy, thio, amino, nitro, cyano or alkyl;
V is a phenyl group;
U is a group of from 0 to 3 atoms other than hydrogen, and is oxy, thio, amino, nitro, cyano, halo or alkyl; and
u is 0 to 3.

22. A method according to claim 21, wherein the non-peptide organic molecule is of formula (1).

23. A method according to claim 22, wherein the non-peptide organic molecule is of the formula:

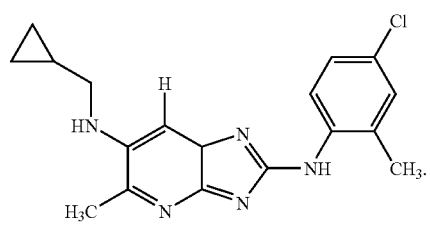

24. A method of modulating the response to a stimulus of hematopoietic or neuronal cells influenced by the binding of EPO to EPO-R, the method comprising:
contacting said cells with an effective amount to modulate said response of a non-peptide organic molecule of from 12 to 36 atoms other than hydrogen, from 9 to 20 carbon atoms, from 4 to 12 of the heteroatoms chalcogen, nitrogen, halogen, and metal ion of Groups I or II of the periodic chart,
wherein said non-peptide organic molecule is of the formula:

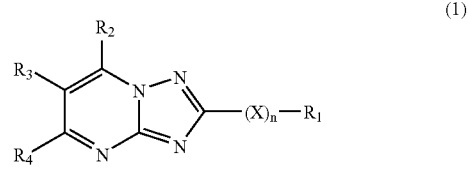

(1)

wherein:

X is of from 1 to 3 atoms other than hydrogen, and is amino, alkyl substituted amino, oxygen, or sulfur bonded to 0 to 2 oxygen atoms;

n is 0 or 1;

$R_1$ is alkyl of from 1 to 3 carbon atoms, substituted phenyl having from 0 to 3 substituents that are $CH_3$, Cl, $NO_2$, or $CF_3$, and $R_1$ is bonded directly to an annular carbon atom or through a linking group of from 1 to 3 carbon and nitrogen atoms in a chain, or N-hydroxamidinyl;

$R_2$ is $CH_3$, $NH_2$, OH, or aroylamido of from 7 to 8 carbon atoms having from 0 to 2 substituents that are $CH_3$, Cl, $NO_2$, or $CF_3$;

$R_3$ is H, carboxy, or cycloalkylalkyl of from 4 to 8 carbon atoms, having from 3 to 4 annular atoms;

$R_4$ is H, unsubstituted or halo substituted lower alkyl of from 1 to 3 carbon atoms, or alkoxymethyl of from 2 to 4 carbon atoms;

with the proviso that $R_3$ and $R_4$ may be taken together to define 1,2-dimethylene-alpha-halo, or alpha-$CH_3$-halobenzene, where halo is F or Cl; or

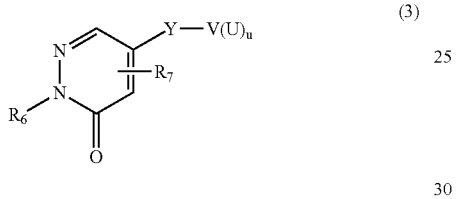
(3)

wherein:

Y is amino, $CH_2$, O, or $S(O)_m$, where m is 0, 1 or 2;

$R_6$ is H or alkyl of from 1 to 3 carbon atoms;

$R_7$ is H, or a group of from 0 to 3 atoms other than hydrogen, and is oxy, thio, amino, nitro, cyano or alkyl;

V is a phenyl group;

U is a group of from 0 to 3 atoms other than hydrogen, and is oxy, thio, amino, nitro, cyano, halo or alkyl; and u is 0 to 3.

25. A method for modulating the activity of EPO-R, present in a cell membrane component, comprising:

forming an EPO-R: non-peptide organic molecule complex in said cell membrane by contacting said EPO-R with an effective amount of a non-peptide organic molecule of from 12 to 36 atoms other than hydrogen, from 9 to 20 carbon atoms, from 4 to 12 of the heteroatoms chalcogen, nitrogen, halogen, and metal ion of Groups I or II of the periodic chart, wherein said non-peptide organic molecule is of the formula:

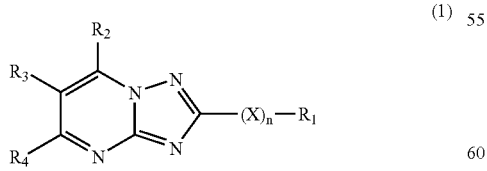
(1)

wherein:

X is from 1 to 7 atoms other than hydrogen, and is amino, alkyl substituted amino, oxygen, or sulfur bond bonded to 0 to 2 oxygen atoms;

n is 0 or 1;

$R_1$ is H or an organic group of from 1 to 12 carbon atoms and from 0 to 6 heteroatoms, which are chalcogen, nitrogen, or halogen, said organic group further comprising an aliphatic group of from 1 to 6 carbon atoms having from 0 to 2 sites of unsaturation, non-oxo-carbonyl and the nitrogen and sulfur derivatives thereof, alicyclic group having from 0 to 2 sites of unsaturation, aryl group, heterocyclic group and combinations thereof, where the cyclic structures may have from 1 to 2 rings;

$R_2$ is H, a heterofunctionality having nitrogen and/or chalcogen bonded to annular carbon to which is substituted with an organic group of from 1 to 10 carbon atoms, aryl, alkaryl, aralkyl, and aralkenyl of from 5 to 10 carbon atoms, aroyl of from 6 to 10 carbon atoms, or an organic group bonded through a carbon atom of from 1 to 12 carbon atoms having from 1 to 4 heteroatoms, which are chalcogen, nitrogen, or halogen;

$R_3$ is H or an organic group of from 1 to 10 carbon atoms and from 0 to 4 chalcogen and nitrogen heteroatoms;

$R_4$ is H, alkyl, or substituted alkyl of from 1 to 6 carbon atoms, where the substituents are oxy, amino or halo;

With the proviso that $R_3$ and $R_4$ may be taken together to form a ring with the annular atoms to which they are attached of from 4 to 10 annular atoms and forming from 1 to 2 rings, where the annular atoms are unsubstituted or substituted with halo, alkyl of from 1 to 3 carbon atoms, alkoxy of from 0 to 3 carbon atoms, thioalkyl of from 0 to 3 carbon atoms or alkylamino of from 0 to 4 carbon atoms;

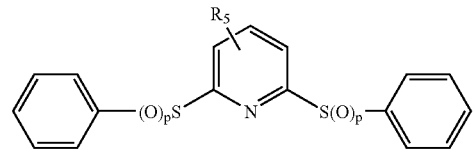
(2)

wherein:

p is 0, 1,or 2;

$R_5$ has from 1 to 3 atoms other than hydrogen, and is oxy, thio, amino, nitro, cyano, or alkyl;

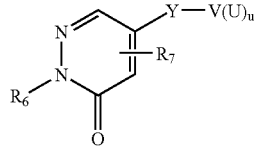
(3)

wherin:

Y is amino, $CH_2$, O, or $S(O)_m$, wherein m is 0, 1, or 2;

V is an aryl group having 6 annular members comprising 0 to 2 nitrogen atoms, the remainder being carbon atoms;

U is a substituent of from 0 to 5 atoms other than H, and is oxy, thio, amino, nitro, cyano, halo, or alkyl;

u is 0 to 3;

$R_6$ is H or alkyl of from 1 to 3 carbon atoms;

$R_7$ is H or a group having 0 to 3 atoms other than H, and is oxy, thio, amino, nitro, cyano, or alkyl; or

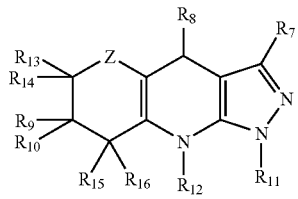
(4)

wherein:
$Z$ is $CH_2$, $C=O$, $C=S$, $C=NH$, or C-alkyl, wherein alkyl is of from 1 to 3 carbon atoms;
$R_7$ is H or an organic group of from 1 to 12 carbon atoms and 0 to 4 heteroatoms;
$R_8$ is H, an aliphatic group of from 1 to 6 carbon atoms, or a heterocycle of from 5 to 6 annular members and from 1 to 2 heteroannular members that are O, N, or S;
$R_9$, $R_{10}$, $R_{13}$, $R_{14}$, $R_{15}$ and $R_{16}$ are the same or different and are H, an organic radical of from 1 to 12 carbon atoms or a heterosubstituent of from 1 to 3 heteroatoms;
$R_{11}$ and $R_{12}$ are the same or different and are H or an organic group of from 1 to 12 carbon atoms.

26. The method of claim 25, wherein the non-peptide organic molecule is of formula (1).

27. The method of claim 25, wherein the non-peptide organic molecule is of formula (2).

28. The method of claim 25, wherein the non-peptide organic molecule is of formula (3).

29. The method of claim 25, wherein the non-peptide organic molecule is a diazolohexahydroquinoline of formula (4).

30. The method of claim 29, wherein said diazolohexahydroquinoline is of the formula:

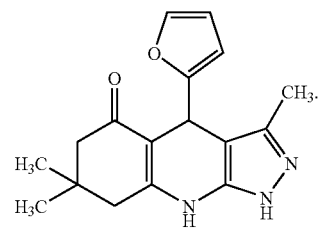

* * * * *